United States Patent
Moult et al.

(10) Patent No.: US 10,839,515 B2
(45) Date of Patent: Nov. 17, 2020

(54) SYSTEMS AND METHODS FOR GENERATING AND DISPLAYING OCT ANGIOGRAPHY DATA USING VARIABLE INTERSCAN TIME ANALYSIS

(71) Applicant: Massachusetts Institute of Technology, Cambridge, MA (US)

(72) Inventors: Eric M. Moult, Cambridge, MA (US); James G. Fujimoto, Medford, MA (US); Stefan B. Ploner, Langensendelbach (DE); Woo J. Choi, Seoul (KR)

(73) Assignee: Massachusetts Institute of Technology, Cambridge, MA (US)

( * ) Notice: Subject to any disclaimer, the term of this patent is extended or adjusted under 35 U.S.C. 154(b) by 134 days.

(21) Appl. No.: 15/964,917

(22) Filed: Apr. 27, 2018

(65) Prior Publication Data
US 2018/0315194 A1    Nov. 1, 2018

Related U.S. Application Data

(60) Provisional application No. 62/491,680, filed on Apr. 28, 2017, provisional application No. 62/491,749, filed on Apr. 28, 2017.

(51) Int. Cl.
*G06K 9/00* (2006.01)
*G06T 7/00* (2017.01)
(Continued)

(52) U.S. Cl.
CPC .......... *G06T 7/0016* (2013.01); *A61B 3/0025* (2013.01); *A61B 3/0041* (2013.01);
(Continued)

(58) Field of Classification Search
CPC ..... A61B 3/0025; A61B 3/0041; A61B 3/102; G06T 2207/10016; G06T 2207/10024;
(Continued)

(56) References Cited

U.S. PATENT DOCUMENTS 7,365,856 B2   4/2008  Everett et al.
8,004,517 B1   8/2011  Edelsbrunner et al.
(Continued)

FOREIGN PATENT DOCUMENTS

EP          1 118 962 A1   7/2001
WO    WO-2006/077107 A1   7/2006
(Continued)

OTHER PUBLICATIONS

Baumann et al., "Total Retinal Blood Flow Measurement with Ultrahigh Speed Swept Source/Fourier Domain ODT," Biomedical Optics Express, 2(6):1539-1552 (2011).
(Continued)

*Primary Examiner* — Xin Jia
(74) *Attorney, Agent, or Firm* — Foley Hoag LLP

(57) ABSTRACT

An imaging (e.g., with an optical coherence tomography system) method that includes 1) acquiring repeated B-scans in a manner consistent with forming images, 2) processing the acquired images according to a variable interscan time analysis (VISTA) method, and 3) generating and displaying a color-mapped image pixel color of the color-mapped image fluid flow speed, or a related quantity.

34 Claims, 18 Drawing Sheets
(6 of 18 Drawing Sheet(s) Filed in Color)

(51) Int. Cl.
A61B 3/00 (2006.01)
A61B 3/10 (2006.01)
G06T 5/50 (2006.01)
(52) U.S. Cl.
CPC ............... *A61B 3/102* (2013.01); *G06T 5/50* (2013.01); *G06T 2207/10016* (2013.01); *G06T 2207/10024* (2013.01); *G06T 2207/10101* (2013.01)
(58) Field of Classification Search
CPC ............ G06T 2207/10101; G06T 5/50; G06T 7/0016
See application file for complete search history.

(56) References Cited

U.S. PATENT DOCUMENTS

| | | | |
|---|---|---|---|
| 9,269,144 B2 | 2/2016 | Kraus et al. | |
| 9,978,159 B2 | 5/2018 | Kraus et al. | |
| 2005/0249398 A1 | 11/2005 | Khamene et al. | |
| 2006/0034374 A1 | 2/2006 | Park et al. | |
| 2008/0021882 A1 | 1/2008 | Pu et al. | |
| 2008/0100612 A1* | 5/2008 | Dastmalchi | A61B 3/0058 345/418 |
| 2009/0005691 A1 | 1/2009 | Huang et al. | |
| 2009/0103049 A1 | 4/2009 | McLean et al. | |
| 2010/0166280 A1 | 7/2010 | Endo et al. | |
| 2010/0208201 A1 | 8/2010 | Knighton et al. | |
| 2011/0075946 A1 | 3/2011 | Buckland et al. | |
| 2011/0134394 A1 | 6/2011 | Srinivasan et al. | |
| 2011/0299034 A1* | 12/2011 | Walsh | A61B 3/0091 351/206 |
| 2014/0160488 A1 | 6/2014 | Zhou | |
| 2016/0284103 A1* | 9/2016 | Huang | G06T 7/62 |
| 2017/0221203 A1* | 8/2017 | Iwase | G06T 7/0012 |
| 2020/0133182 A1* | 4/2020 | Haik | G05B 13/027 |

FOREIGN PATENT DOCUMENTS

| | | |
|---|---|---|
| WO | WO-2011/139895 A1 | 11/2011 |
| WO | WO-2018/204748 A1 | 11/2018 |

OTHER PUBLICATIONS

Braaf et al., "Angiography of the retina and the choroid with phase-resolved OCT using interval-optimized backstitched B-scans," Biomed. Opt. Express (2012).
Choi et al., "Ultrahigh-Speed, Swept-Source Optical Coherence Tomography Angiography in Nonexudative Age-Related Macular Degeneration with Geographic Atrophy," Ophthalmology, (2015).
Choi et al., "Characterizing relationship between optical microangiography signals and capillary flow using microfluidic channels," Biomed. Opt. Express, 7:2709-2728 (2016).
Jaillon et al., "Variable Velocity Range Imaging of the Choroid with Dual-Beam Optical Coherence Angiography," Opt. Express 20:385-396 (2012).
Kraus et al., "Combination of Multiple Motion Corrected OCT Volume Scans for Noise Reduction and Extraction of Arbitrary Cross-Sectional Images," ARVO Abstract Only, 2 pages, Retrieved from the Internet on Feb. 16, 2010 from http://www.abstractsonline.com/submit/SubmitPrinterFriendlyVersion.as . . . .
Kraus et al., "Motion Artifact Correction in OCT Volume Scans Using Image Registration," ARVO Abstract Only, 3 pages, Retrieved from the Internet on Apr. 12, 2009 from http://www.abstractsonline.com/submit/SubmitPrint . . . .
Lee, J. et al., "Dynamic light scattering optical coherence tomography," Opt. Express, 20:22262-22277 (2012).
Notification Concerning Transmittal of International Preliminary Report on Patentability and International Preliminary Report on Patentability for Int'l Application No. PCT/US2011/034572, "Method and Apparatus for Motion Correction and Image Enhancement for Optical Coherence Tomography," dated Nov. 8, 2012.
Notification of Transmittal of the International Search Report and the Written Opinion of the International Searching Authority for Int'l Application No. PCT/US2011/034572; 13 pages, dated Sep. 14, 2011.
Ricco et al., "Correcting Motion Artifacts in Retinal Spectral Domain Optical Coherence Tomography via Image Registration," Medical Image Computing and Computer-Assisted Intervention a Miccai 2009, Springer Berlin Heidelberg, Berlin, Heidelberg, pp. 100-107, XP019130304 (2009).
Shi et al., "Wide Velocity Range Doppler Optical Microangiography Using Optimized Step-Scanning Protocol with Phase Variance Mack," Journal of Biomedical Optics, 18(10):106015 (2013).
Tokayer et al., "Blood Flow Velocity Quantification Using Split-Spectrum Amplitude-Decorrelation Angiography with Optical Coherence Tomography," Biomedical Optics Express 4:1909-1924 (2013).
Tolliver et al., Carnegie Mellon, UPMC Eye Center "An In-painting Method for Combining Multiple SD-OCT Scans With Applications in Z-Motion Recovery," Noise Reduction and Longitudinal Studies, Tuesday, May 5, 2009, 1 page.
Zawadzki et al., "Correction of motion artifacts and scanning beam distortions in 30 ophthalmic optical coherence tomography imaging," Progress in Biomedical Optics and Imaging, Proceedings of SPIE—Ophthalmic Technologies XVII 2007 SPIE US, 6426:1-11 (2007).
International Search Report and Written Opinion for International Application No. PCT/US2018/031030 dated Oct. 3, 2018.
Jonghwan et al., "Dynamic light scattering optical coherence tomography," Opt. Express, 20:22262-22277 (2012).

* cited by examiner

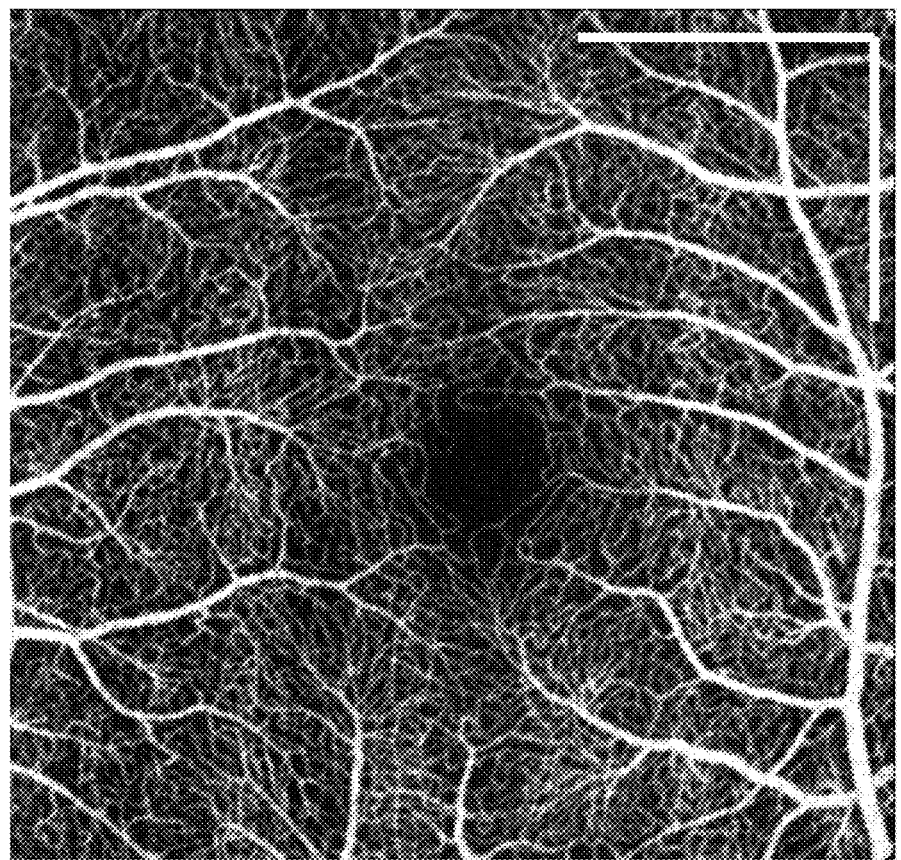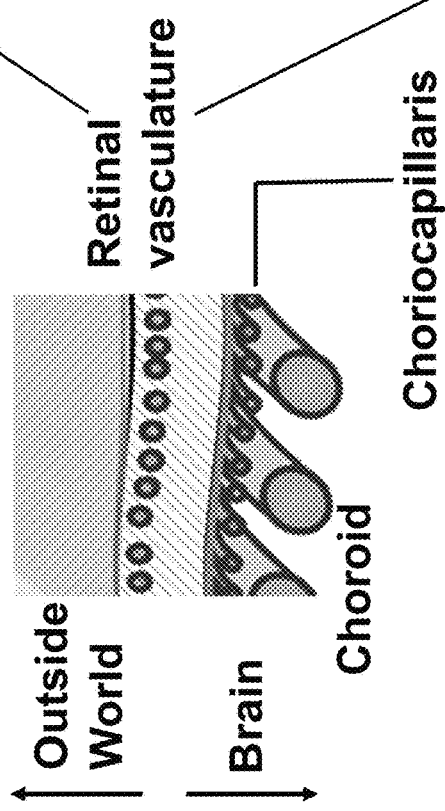
FIG. 2

$$D(B_i, B_j) = 1 - \frac{\min(B_i, B_j)}{\max(B_i, B_j)},$$

$$S = \begin{pmatrix} 0 & 1 & 1 & 0 \\ 0 & 0 & 1 & 1 \\ 0 & 0 & 0 & 1 \\ 0 & 0 & 0 & 0 \end{pmatrix}$$

$$C = \begin{pmatrix} \blacksquare & \frac{\min(B_1, B_2)}{\max(B_1, B_2)} & \frac{\min(B_1, B_3)}{\max(B_1, B_3)} & \frac{\min(B_1, B_3)}{\max(B_1, B_3)} \\ \blacksquare & \blacksquare & \frac{\min(B_2, B_3)}{\max(B_2, B_3)} & \frac{\min(B_2, B_4)}{\max(B_2, B_4)} \\ \blacksquare & \blacksquare & \blacksquare & \frac{\min(B_3, B_4)}{\max(B_3, B_4)} \\ \blacksquare & \blacksquare & \blacksquare & \blacksquare \end{pmatrix}$$

$$f_2(C) = \frac{\frac{1}{3}\sum \Delta 1 \text{ diagonal}}{\frac{1}{2}\sum \Delta 2 \text{ diagonal}}$$

FIG. 11

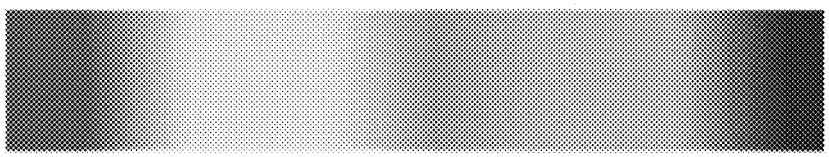
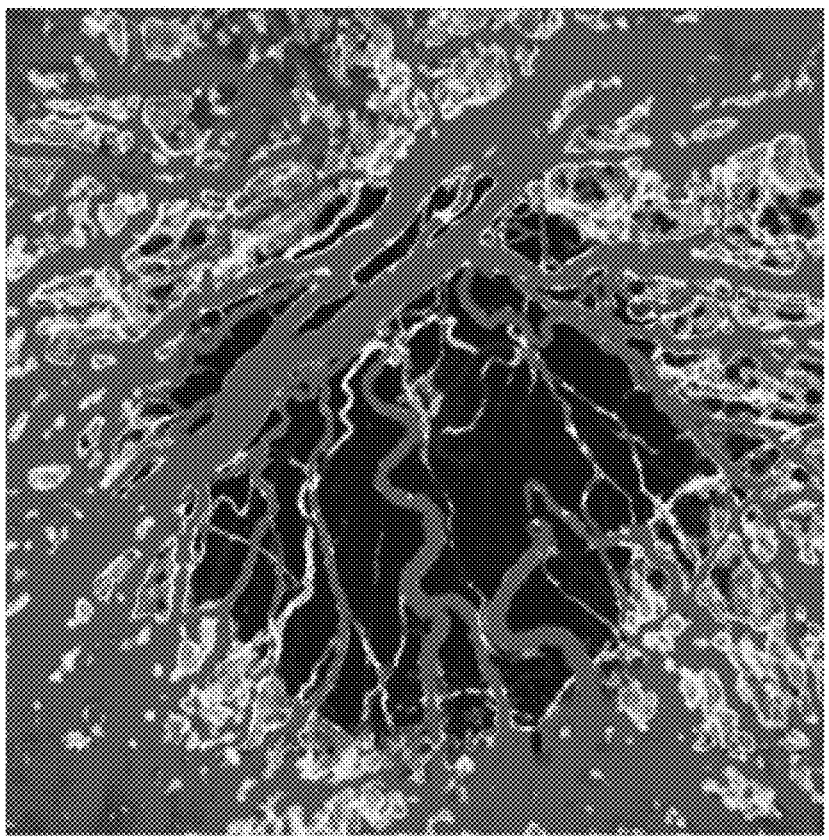
FIG. 12

SYSTEMS AND METHODS FOR GENERATING AND DISPLAYING OCT ANGIOGRAPHY DATA USING VARIABLE INTERSCAN TIME ANALYSIS

CROSS-REFERENCE TO RELATED APPLICATIONS

This application claims priority to U.S. Provisional Application Ser. No. 62/491,680, filed on Apr. 28, 2017, entitled "VARIABLE INTERSCAN TIME ANALYSIS SYSTEM"; and to U.S. Provisional Application Ser. No. 62/491,749, filed on Apr. 28, 2017, entitled "VARIABLE INTERSCAN TIME ANALYSIS SYSTEM," the entireties of which are incorporated herein by reference.

GOVERNMENT LICENSE RIGHTS

This invention was made with government support under grant number FA9550-12-1-0499 and FA9550-15-0473 awarded by the Air Force Office of Scientific Research (AFOSR), and R44-EY022864 and R01-EY011289 awarded by the National Institutes of Health (NIH). The government has certain rights in the invention.

RELATED REFERENCES

"Toward Quantitative Optical Coherence Tomography Angiography: Visualizing Blood Flow Speeds in Ocular Pathology Using Variable Interscan Time Analysis," Ploner et al., Retina, Vol. 36, No. 12, Supplement 1, pages S118-S126, December 2016, is herein incorporated by reference.

BACKGROUND

A variety of ocular pathologies are caused by and/or result in alterations of the retinal and/or choriocapillaris vasculatures. For example, age-related macular degeneration (AMD) and diabetic retinopathy (DR), leading causes of blindness and severe vision loss in developed countries, are associated with alterations of the retinal and choriocapillaris vasculatures. Retinal and choroidal vasculatures have traditionally been imaged with dye-based methods, such as fluorescein angiography and indocyanine green angiography. More recently, optical coherence tomography (OCT) angiography (OCT-A) has emerged as a noninvasive method for volumetrically visualizing retinal and choroidal vasculatures in vivo.

SUMMARY OF THE INVENTION

The present disclosure is thus directed to improved vasculature display methods. For example, according to a first example of the disclosure herein, an imaging method comprises acquiring data of at least three repeated B-scan images of a same location, wherein the at least three repeated B-scan images is acquired at an interscan time interval; generating at least two images based on the acquired data, wherein a first of the at least two images is a composite of the acquired data according to the interscan time interval, and a second of the at least two images is a composite of the acquired data according to a multiple of the interscan interval; generating a color-mapped image based on the at least two images, wherein pixel brightness and pixel color of the color-mapped image each represent one of blood flux and blood flow speed; and displaying the color-mapped image.

According to various embodiments of the above example, the data of the at least three repeated B-scan images is acquired in a single scan pattern; the data of the at least three repeated B-scan images is acquired with an optical coherence tomography system; the pixel brightness is determined by: performing, on a pixel-by-pixel basis, a decorrelation operation on the at least two images, thereby generating a brightness decorrelation image; adjusting a contrast of the brightness decorrelation image by remapping pixel intensities in predefined quantiles to an upper value or to a lower value, and remapping remaining pixel intensities to values between the upper value and the lower value; and masking vasculature of the at least two images and applying the masked vasculature to the brightness decorrelation image having the adjusted contrast as a binary mask, thereby setting pixel intensities that do not correspond to vasculature to the upper value or the lower value, wherein brightness at each pixel of the color-mapped image is based on the pixel intensities; the pixel color is determined by: calculating, on a pixel-by-pixel basis, a ratio of the at least two images, thereby generating a color decorrelation image; filtering the color decorrelation image; and remapping pixel intensities of the color decorrelation between predetermined high and low values, wherein color at each pixel of the color-mapped image is based on the pixel intensities; the color-mapped image is displayed as an overlay on a corresponding image; and/or the at least two images are angiographic images.

According a second example, an imaging method comprises acquiring data of at least three repeated B-scan images of a same location, wherein the at least three repeated B-scan images is acquired at an interscan time interval; generating at least two images according to a variable interscan time analysis method, each of the at least two images being generated according to a different interscan time; generating a brightness decorrelation image by performing, on a pixel-by-pixel basis, a decorrelation operation on the at least two images; generating a color decorrelation image by calculating, on a pixel-by-pixel basis, a ratio between the at least two images; generating a color-mapped image based on the brightness decorrelation image and the color decorrelation image; and displaying the color-mapped image, wherein pixel brightness and pixel color of the color-mapped image each represent one of blood flux and blood flow speed.

According to various embodiments of the above example, the data of the at least three repeated B-scan images is acquired in a single scan pattern; the data of the at least three repeated B-scan images is acquired with an optical coherence tomography system; the color-mapped image is displayed as an overlay on a corresponding image; the at least two images are angiographic images.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 is an example OCT-A image flattened along the retinal depth direction as a mean en face projection;

FIGS. 10 and 11 schematically show a second example VISTA function;

FIG. 12 is an example color-mapped VISTA image;

DETAILED DESCRIPTION

Optical Coherence Tomography Angiography (OCT-A)

Figure 1:
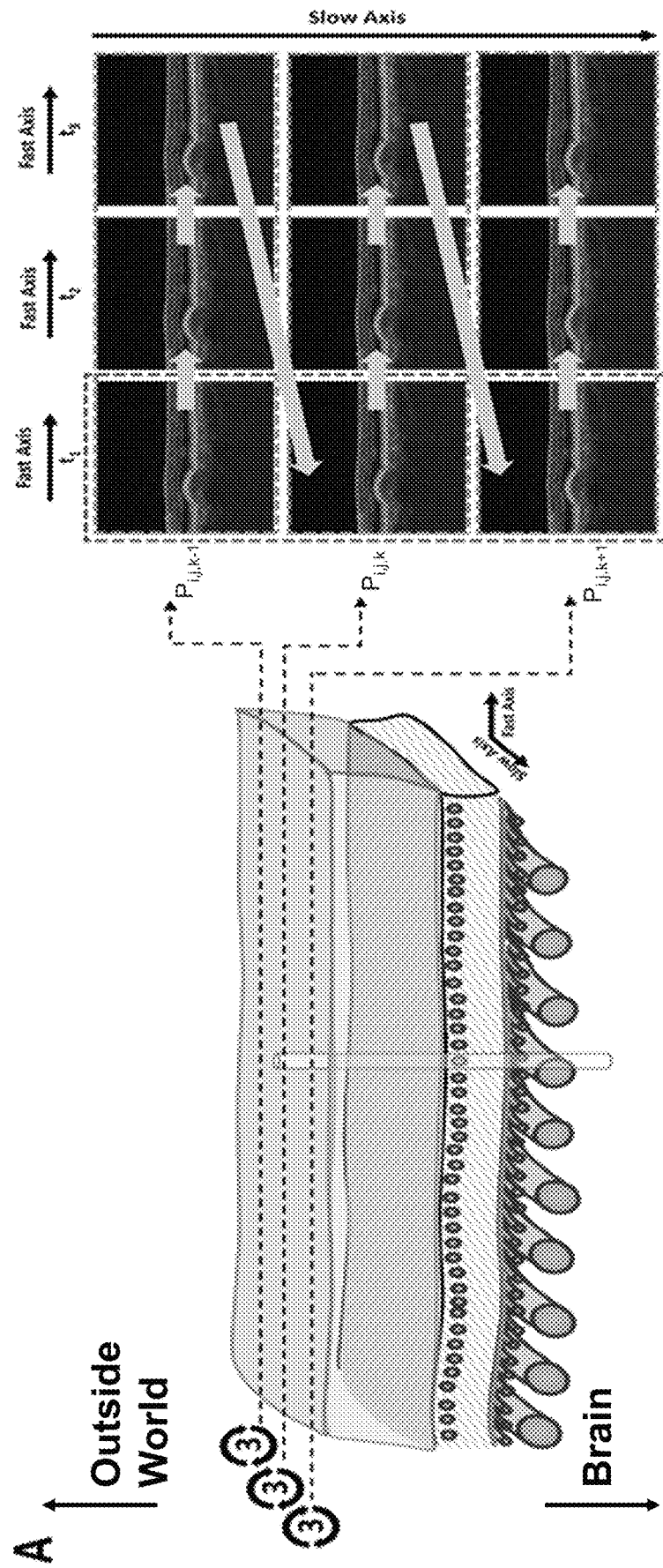
FIG. 1 illustrates an example optical coherence tomography angiography (OCT-A) scanning protocol.

Optical coherence tomography angiography (OCT-A) has its roots in Doppler OCT, a technique that measures the Doppler shifts caused when blood cells scatter the OCT light beam. FIG. 1 illustrates an example optical coherence tomography angiography (OCT-A) scanning protocol. Therein, a typical OCT-A acquisition involves acquiring, for each slow axis B-scan position, repeated OCT B-scans ($P_{i,j}$). The beam can then be translated along a "slow axis" so as to acquire sets of repeated from different slow axis positions. In this way an OCT-A volume can be generated. The resulting B-scans can be schematically arranged in the image matrix shown in FIG. 1, where the thick arrows through the matrix indicate time progression.

While FIG. 1 illustrates a simple raster scanning protocol, OCT-A can be performed using a wide range of acquisition protocols. For example, repeated B-scans may be acquired radially, and the B-scan position may be rotated about some point. Furthermore, while in the example of FIG. 1, three repeated B-scans are at each slow axis position, the only requirement in OCT-A is that more than one repeated B-scans be acquired.

As used herein, "B-scan" means a collection of two or more A-scans taken from distinct positions. Because the OCT light beams have a physical transverse width (the spot size), the optical fields from two distinct A-scan positions may overlap. This can happen, for example, in the case of oversampled scanning, which is commonly performed in OCT-A. As used herein, "repeated B-scans" means a collection of two or more B-scans in which at least one A-scan is common to all B-scans in the collection. It is noted that this meaning may be broader than that used in some literature.

OCT-A is based on the idea that if the imaged tissue is stationary between repeated scans, the repeated B-scans will be identical, or very similar. If there is movement within the tissue, the repeated B-scans will differ due to this movement. In biological tissue, and in particular ocular tissue, this difference between repeated B-scans is often caused by moving blood cells, and can thus be used as an indicator of blood flow. Because blood flow is, typically, localized to vasculature, an OCT-A image of blood flow also delineates vascular structure. When applied to ophthalmological imaging, the OCT-A can generate images of ocular vasculatures (for example, retinal and choroidal vasculatures).

An example OCT-A image of the retinal vasculature of a normal subject, flattened along the retinal depth direction, is illustrated in FIG. 2. Such a projection along the axial direction, parallel to the OCT beam, is referred to as an en face projection. The field of view of the OCT-A image in FIG. 2 is 3 mm×3 mm, and is centered at the fovea.

In an OCT-A acquisition, the time between repeated A-scans in a collection of repeated OCT B-scans is herein referred to as the "interscan time" (denoted by $\Delta t$, or multiples thereof). The interscan time determines the sensitivity and saturation of the OCT-A signal versus blood flow speed. Longer interscan times detect slower flow speeds, but result in saturated OCT-A signals if flow is fast. Shorter interscan times can differentiate between these faster flows, generally show reduced OCT-A signals, and may not detect blood flows having slower speeds. Flow sensitivity is also affected by parasitic eye motion. For example, saccades and other eye motion can result in high OCT-A signal even in the absence of blood flow.

Figure 3:
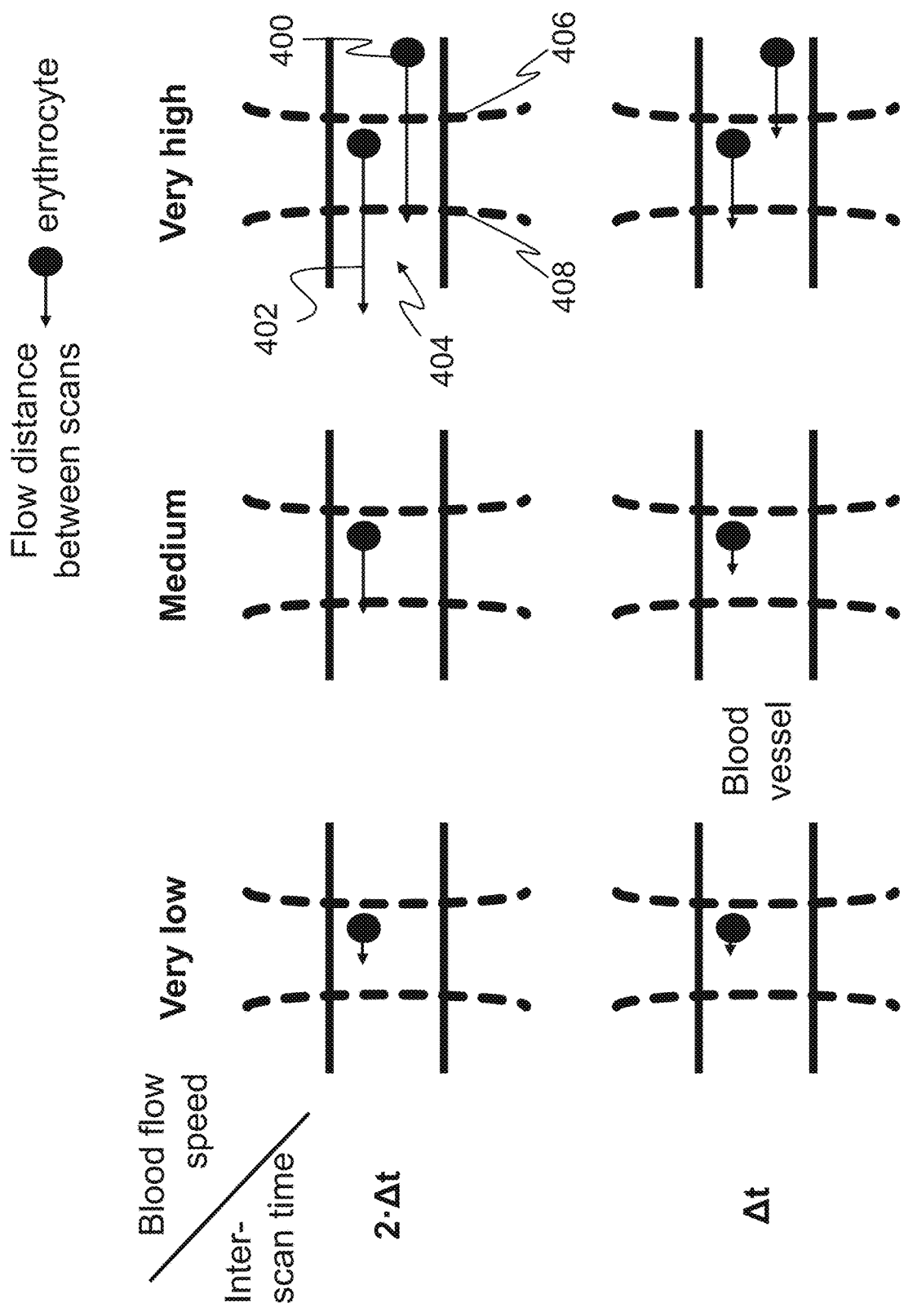
FIG. 3 schematically illustrates the relationship between interscan time and flow distance.
Figure 4:
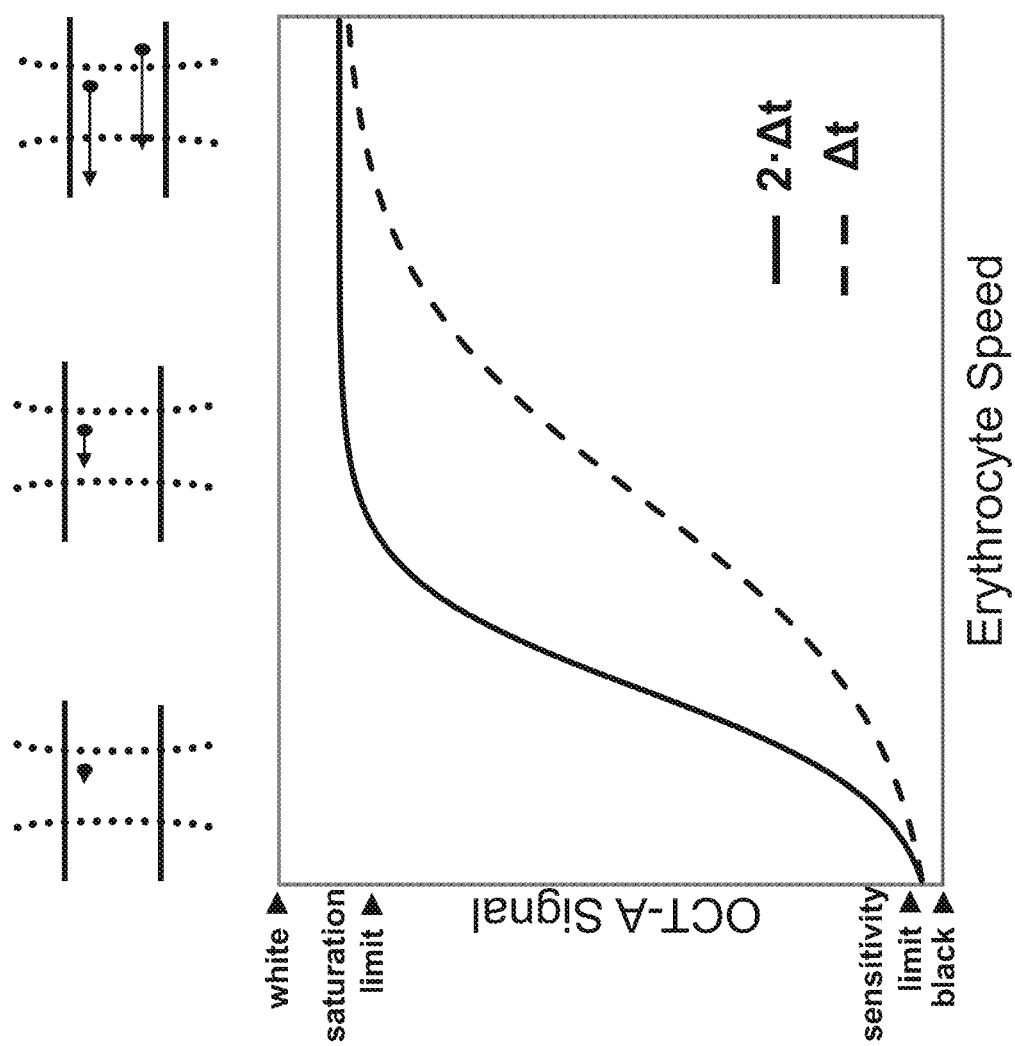
FIG. 4 is a graph illustrating the relationship between interscan time and flow distance on sensitivity and saturation of an OCT-A signal.
Figure 5:
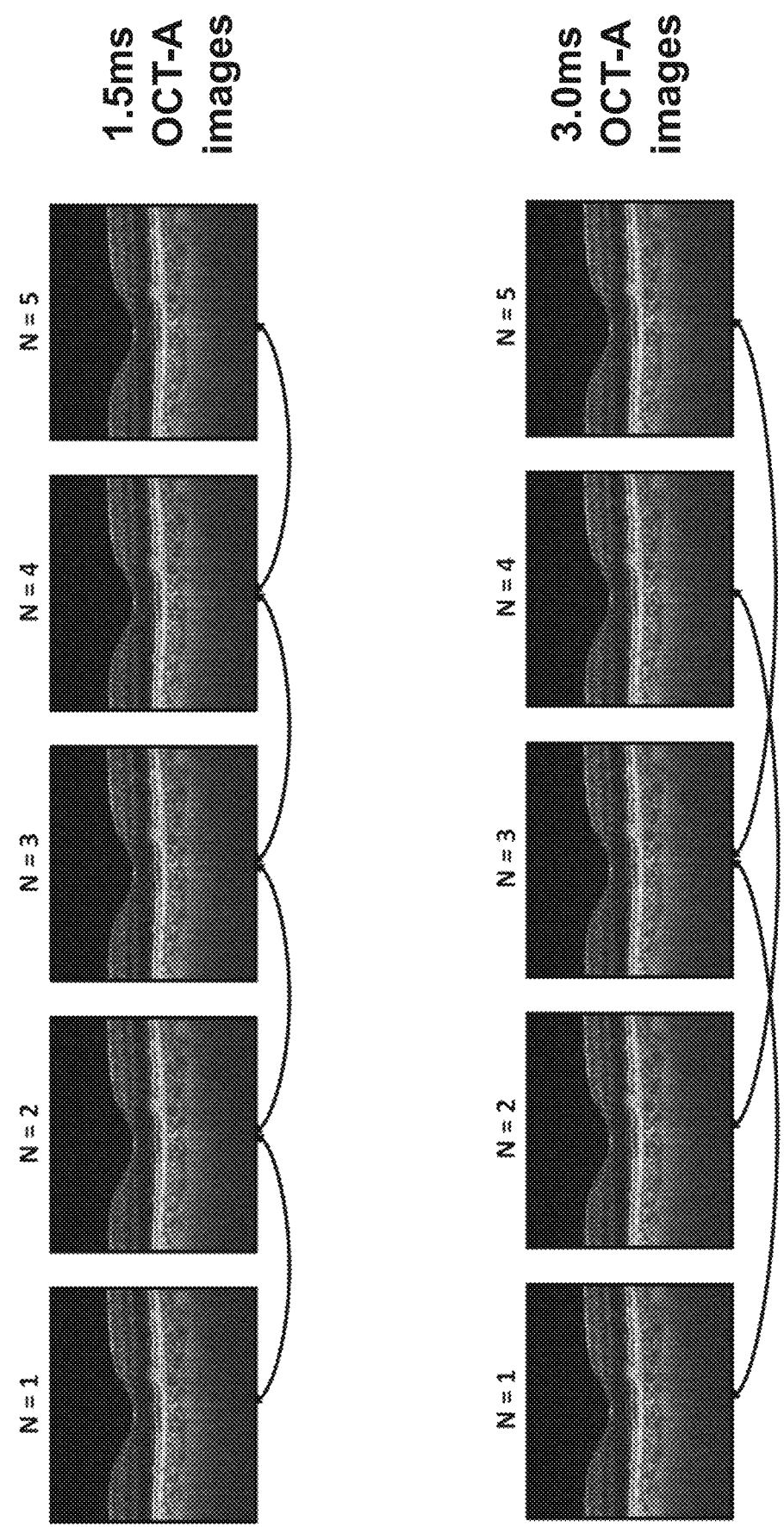
FIG. 5 illustrates comparison of the same repeated B-scans to form OCT-A images based on multiple interscan times.

The OCT-A signal level depends on the interscan time in, approximately, the same way as it depends on the blood cell speed. For example, doubling the interscan time will result in, approximately, the same change in an OCT-A signal as doubling the blood cell's speed. This relationship can be exploited to estimate a blood cell's speed. This relationship between interscan time, blood flow speed, and blood cell displacement is schematically illustrated in FIGS. 3 and 4. Therein, FIG. 3 schematically illustrates the relationship between interscan time and flow distance for three flow distances (very low, medium, and very high) during two interscan times ($\Delta t$ and ½ $\Delta t$). Therein, each erythrocyte 400 is shown as traveling a relative distance 402 in a blood vessel 404 between OCT beams 406, 408 separated by the interscan time. Simply, the flow distance during the interscan time is illustrated as the length of the arrow leading from each erythrocyte. The effect of this relationship on an OCT-A signal is illustrated in the graph of FIG. 5, plotting an OCT-A signal against erythrocyte speed. As can be seen in the graph, the three relative flow distances 502, 504, 506 correspond with three speeds (the slower an erythrocyte moves, the shorter the distance traveled during a given interscan time). A longer interscan time ($\Delta t$) causes the resulting OCT-A signal to reach a saturation point at a lower erythrocyte speed; however a shorter interscan time (½ $\Delta t$) is less sensitive (showing less change in an OCT-A signal value) at slower erythrocyte speeds.

OCT-A is a promising modality for visualizing vasculature (e.g., presence, absence, or morphological alterations) in a variety of ocular diseases, including age-related macular degeneration and diabetic retinopathy. Compared to dye-based techniques, OCT-A is depth-resolved, non-invasive, acquired simultaneously with OCT, capable of resolving microvasculature, capable of visualizing retinal and choriocapillaris vasculatures, not obfuscated by dye leakage, and potentially quantitative. However, most OCT-A techniques have limited dynamic ranges, and provide and display limited information about the blood flow speeds within the imaged vasculature. Visualizing blood flow speeds, and related quantities, may be important when assessing diseases in which disease progression is linked to flow impairment, not just vasculature loss or morphological alterations. It may also be useful for assessing treatment responses, detecting diseases at early or sub-clinical stages, and/or for developing and/or evaluating endpoints for pharmaceutical trials. For example, a patient with choroidal neovascularization (CNV) may be injected with vascular endothelial grow factor inhibitors for treatment. Visualization and/or quantitation of the blood flow speeds and/or related quantities within, or surrounding, the lesion before and after injection may be useful for determining treatment efficacy, individualizing treatment strategies, and so on.

Blood flow speeds may also be used for tracking the natural progressions of diseases that are caused by, and/or result in, blood flow alterations. For example, knowledge of blood flow speeds may be useful for studying the relationship between the development/growth of geographic atrophy and choriocapillaris alterations. Or, as another example, knowledge of blood flow speeds may be useful for investigating possible relationships between neurodegenerative diseases, such as Alzheimer's disease, and blood flow speeds in the vasculature of the eye or brain. While there have been some proposed approaches to quantitate the OCT-A signal, OCT-A images are currently interpreted by most clinicians as showing the presence or absence of vasculature, rather than as showing data relating to blood flow speeds, with the OCT-A images interpreted in an almost binary manner. Thus, typically, OCT-A images are currently used to delineate vascular structures, rather than to provide information about blood flow within these vascular structures.

Variable Interscan Time Analysis (VISTA)

Variable interscan time analysis (VISTA) methods examine, using a single acquisition of more than two repeated B-scans, the blood flow speed, velocity, or related quantities, by exploiting the dependency of the OCT-A signal/image on the interscan time. In particular, VISTA involves computing, from a single acquisition of repeated B-scans, OCT-A images corresponding to different interscan times, or data formed by exploiting the dependency of the OCT-A signal on the interscan time, and then interpreting the differences in these images/data as being related to blood flow speed, velocity, or related quantities.

For example, as illustrated in FIG. 5, OCT-A images corresponding to different interscan times can be generated using a single acquisition of repeated B-scans by acquiring five repeated B-scans at each slow scan position. In particular, comparing temporally adjacent images provides OCT-A data corresponding to the fundamental interscan time (1.5 ms in this case). Comparing "every other" temporal image provides a comparison of images according to a time equal to twice the fundamental interscan time (3.0 ms in this case). In this example, a fixed fundamental interscan time (1.5 ms) is used; however, as noted previously, the fundamental interscan time need not need remain fixed during the scan. For example, there could be a 3 repeated B-scan protocol in which the interscan time between the first and second repeated B-scans is 1.5 ms, while that between the second and third is 3.0 ms. In this case, the effective interscan time between the first and third repeated OCT B-scans would be 4.5 ms.

Figure 6:
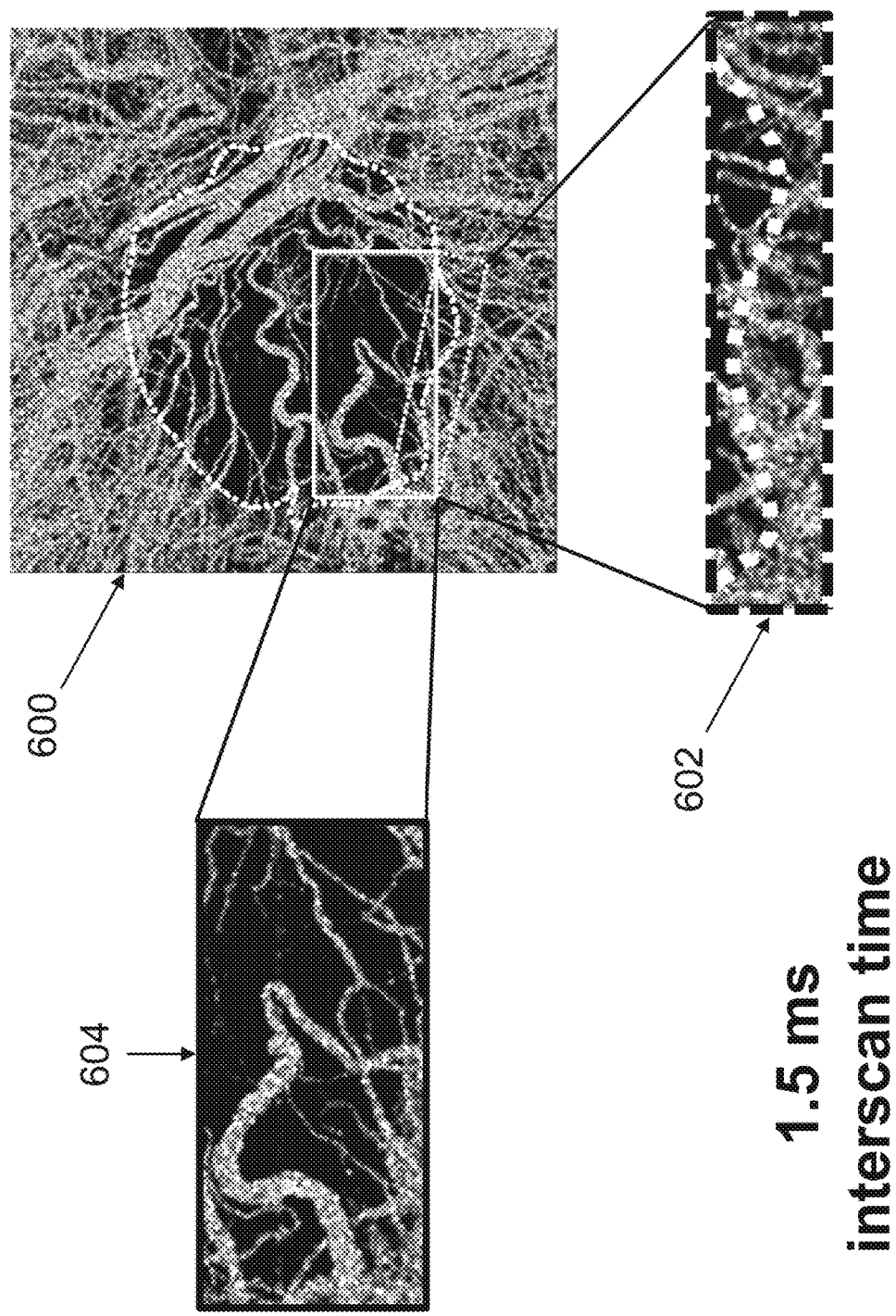
FIG. 6 illustrates an en face OCT-A image generated from the 1.5 ms interscan time as shown in FIG. 5.
Figure 7:
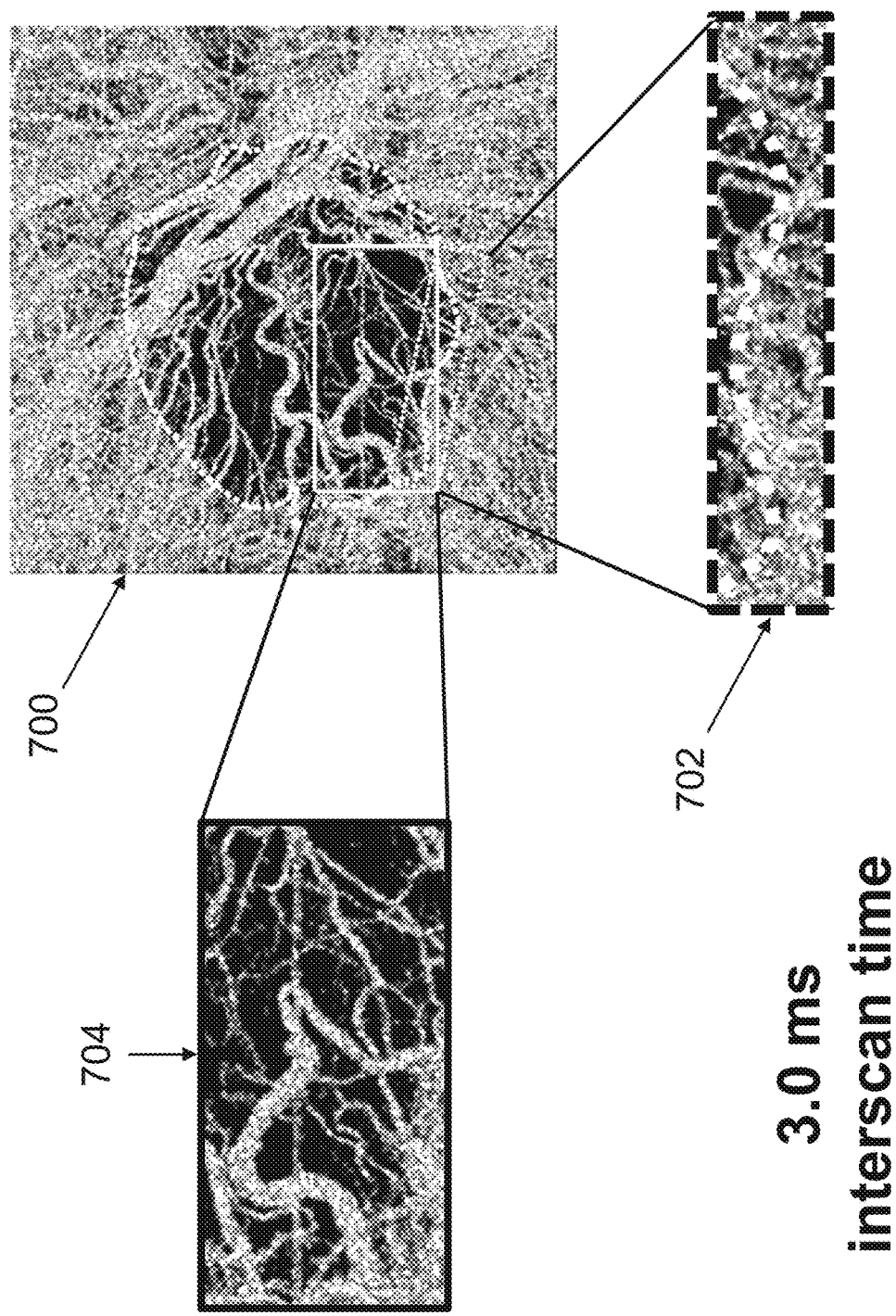
FIG. 7 illustrates an en face OCT-A image generated from the 3.0 ms interscan time as shown in FIG. 5.

The effects of varying the interscan time in this manner are illustrated, for example, in FIGS. 6 and 7, which show two en face OCT-A images (1.5 ms interscan time shown in FIG. 6 and 3.0 ms interscan time shown in FIG. 7) generated using the method of FIG. 5. In particular, OCT-A signals for the images in FIGS. 6 and 7 were generated by performing a decorrelation operation, on a pixel-by-pixel basis, between sequential OCT B-scans (N=1↔2, 2↔3, 3↔4, and 4↔5) corresponding to a fundamental interscan time of 1.5 ms, and between "every other" scan (N=1↔3, 2↔4, 3↔5) corresponding to an effective interscan time of 3.0 ms.

According to this example, the "decorrelation" of two pixel values $v_1$ and $v_2$, was determined according to the operation $(v_1-v_2)^2/(v_1^2+v_2^2)$. However, this analysis could be performed using comparison operations other than decorrelation; for example, a ratio operation according to $1-[\min(v_1, v_2)/\max(v_1, v_2)]$ may also be used. Other comparison operations, sensitive to OCT amplitude, OCT phase, or a combination of phase and amplitude may be used in still other embodiments. Optical micro-angiography (OMAG), or related functions such as complex-OMAG ($OMAG^c$), may be used. Split-spectrum amplitude-decorrelation angiography (SSADA) could also be used. Indeed, any comparison could be used and the specific operation is not central to VISTA methods.

Further, it is noted that the operations need not be performed on a pixel-by-pixel basis. In some embodiments it may be possible to perform the operation on groups of pixels. It is also noted that in the examples of FIGS. 6 and 7, intermediate OCT-A images generated by pairwise comparisons were grouped by interscan time (e.g., as either corresponding to a 1.5 ms interscan time or a 3.0 ms interscan time). Then the B-scans in these groups were averaged to improve the signal-to-noise ratio and also to minimize statistical fluctuations (statistical fluctuations may be caused by the stochastic nature of the blood flow and/or the stochastic nature of optical light scattering and/or light/electronic detection, or other factors). Examining the differences in the 1.5 ms and 3.0 ms OCT-A images (600 and 700) of FIGS. 6 and 7, respectively, it can be seen that there is an OCT-A signal in the 3.0 ms image that is not present in the 1.5 ms image. In the dashed-line enlargements (602 and 702), this increased OCT-A signal is visible at the edges of the margin of geographic atrophy, and indicates a slower blood flow, but not necessarily complete dysfunction/atrophy of the choriocapillaris. In the solid-line enlargements (604 and 704), the 3.0 ms OCT-A image 700 reveals certain vasculature which is not apparent, or not as readily apparent, in the 1.5 ms OCT-A image 600. This illustrates that the OCT-A signal is dependent on the interscan time, and that different interscan OCT-A images can be formed from a single repeated B-scan acquisition to convey information related to blood flow speed and related quantities.

To minimize the effects of bulk inter-B-scan eye and/or system motion, which produces spurious decorrelation signals, the repeated B-scans can be motion corrected using, for example, a speckle preserving rigid registration algorithm, as was done in the computation used to generate FIGS. 6 and 7, before calculating decorrelation. Non-rigid registrations can also be used.

VISTA Functions

Although side-by-side comparison of two or more OCT-A images corresponding to different interscan times, as done in FIGS. 6 and 7, can be useful for making basic statements about blood flow speed, it can complicate the interpretation, require detailed visual analysis, does not necessarily make apparent subtle variations, and may not be well-suited to quantitation. Therefore, the clinical applicability of displaying OCT-A data corresponding to multiple interscan times in such a manner can be limited. To overcome these difficulties, VISTA functions and VISTA color mapping are described herein.

Herein, a VISTA function may be a process that:
1) takes, as its input, a sequence of three or more repeated OCT B-scans acquired from the same location of an object (e.g., having vasculature or otherwise subject to motion contrast);
2) generates an ordered collection of pairwise comparisons between these repeated B-scans; and
3) based on the ordered collection, generates as its output, one or more images that represent motion contrast (e.g., are associated with blood flow speed (the speed blood cells through a blood vessel or other vasculature), blood flow velocity (the speed and direction (velocity) of blood cells through a blood vessel or other vasculature), blood flow flux (a number of blood cells that flow through a cross-sectional area of a blood vessel or other vasculature), or some quantity related to blood flow through vasculature),
4) where re-arranging or permuting the order of the pairwise comparisons changes the generated output.

Mathematically, this may be expressed in one form as:
Let $\mathcal{B}$ be the set of all possible B-scans, where each B-scan has $n_z$ rows and $n_x$ columns.
Let a repeated OCT B-scan acquisition be mathematically represented by the sequence: $\mathcal{B}^N \ni (B)_i = (B_1, B_2, \ldots, B_N)$ where $B_k \in \mathcal{B}$ with $1 \leq i \leq N$.
Set $N \geq 3$.
Let $\mathcal{S}$ be the set of all N×N binary matrices (i.e., $S=\{1, \ldots, N\} \times \{1, \ldots, N\} \to \{0,1\}$).
Let $\mathcal{D}$ be the set of all "pairwise comparison" functions: $\mathcal{D} \ni D: \mathcal{B} \times \mathcal{B} \to \mathbb{F}^{n_z \times n_x}$, where $\mathbb{F}$ is some arbitrary set of outcomes (e.g., $\mathbb{F}=\mathbb{R}, \mathbb{C}, \{1, \ldots 2^{16}-1\}$).
Let $\mathcal{C}$ be the set of all N×N matrices over $\mathbb{F}^{n_z \times n_x} \cup \{\Box\}$ where: 1) $\Box$ is some arbitrary additional element, analogous to writing the extended reals as $\mathbb{R} \cup \{\infty\}$; 2) $\mathbb{F}^{n_z \times n_x} \cap \{\Box\} = \emptyset$; and 3) $\mathcal{C}$ is a matrix whose elements are also matrices (OCT-A B-scans).
Define $F_1$ as the set of functions of the following form:

$f_1: (\mathcal{B}^N, \mathcal{S}, \mathcal{D}) \to \mathbb{F}$ $((B)_i, S, D) \mapsto C$ where the (i,j)-th component of C is given by:

$$C_{i,j} = \begin{cases} \Box & \text{if } S(i,j) = 0 \\ D(B_i, B_j) & \text{else} \end{cases}$$

Define $\mathcal{F}_2$ as the set of functions $\mathcal{F}_2 \ni f_2: \mathcal{F} \to \mathbb{F}^{n'_z \times n'_x}$, where $n'_z \times n'_x$ are the dimensions of the output image (while it may be that $n'_z = n_z$ and $n'_x = n_x$, this need not be the case; for example, in forming an en face VISTA image, $n'_z = 1$).
Define $P_{\neg\Box}$ as a permutation operation on the matrix $C \in \mathbb{F}$ which re-arranges (i.e., permutes) the non-$\Box$ elements of C.
Define $\mathcal{P}_{\neg\Box}$ as the set of all such permutation operations.
Considering the above definitions, let $f_1 \in \mathcal{F}_1$ and $f_2 \in \mathcal{F}_2$. A VISTA function as used herein is thus defined as a function satisfying the following two properties:
(1) The function is expressible in, or closely related to, the form of $f_2 \circ f_1$
(2) $\exists P_{\neg\Box}, P'_{\neg\Box} \in \mathcal{P}_{\neg\Box}$ such that $f_2 \circ P_{\neg\Box} \circ f_1 \neq f_2 \circ P'_{\neg\Box} \circ f_1$.

It is noted that the above description may not cover all VISTA processes contemplated to be within the scope of the present invention. For example, $f_2$ need not be a "function" in the mathematical sense, or may not be well suited for mathematical description, such as in the case of a complex sequence of steps. For example, $f_2$ may involve a non-deterministic estimation of parameters that correspond to the matrix C. It is also noted that a VISTA function may produce more than one output image, which is not captured in the mathematical description above.

Figure 8:
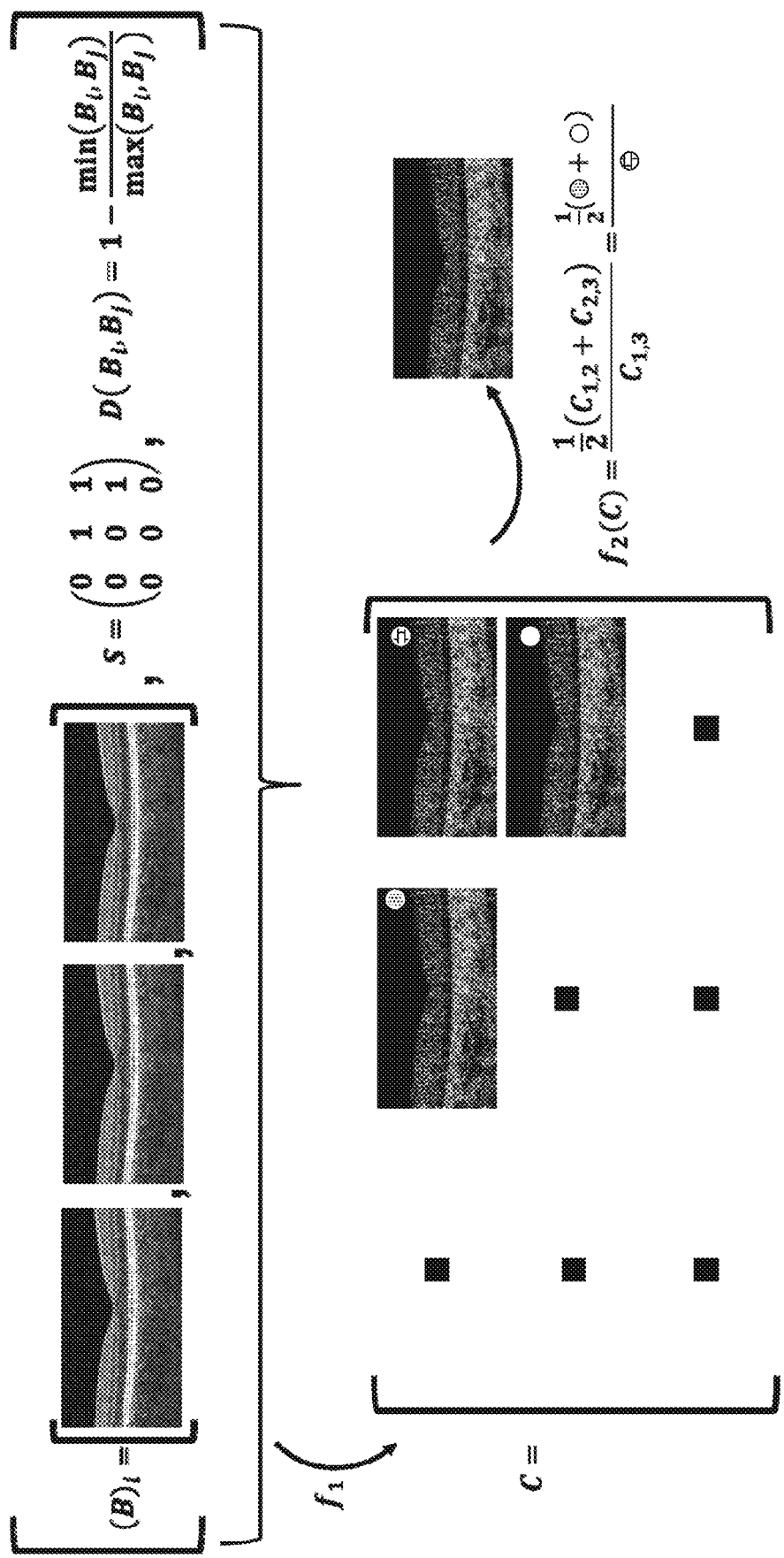
FIGS. 8 and 9 schematically show a first example VISTA function.
Figure 9:
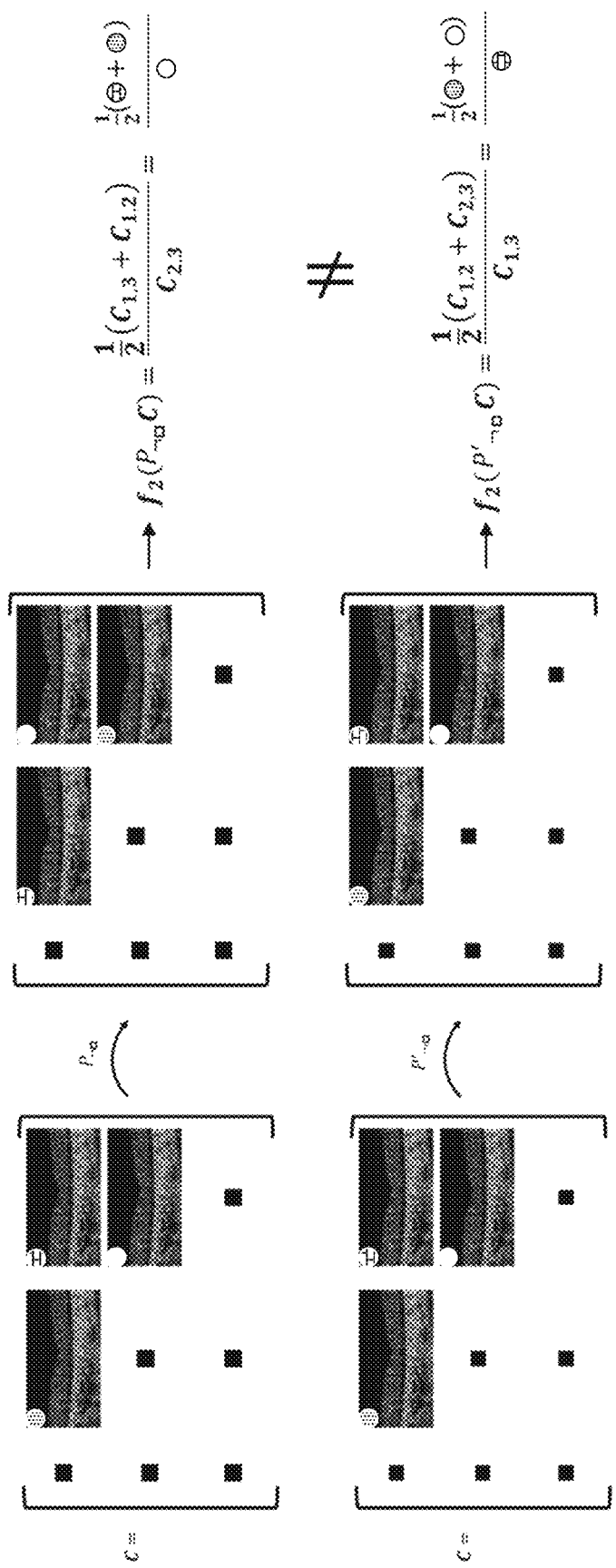
Figure 10:
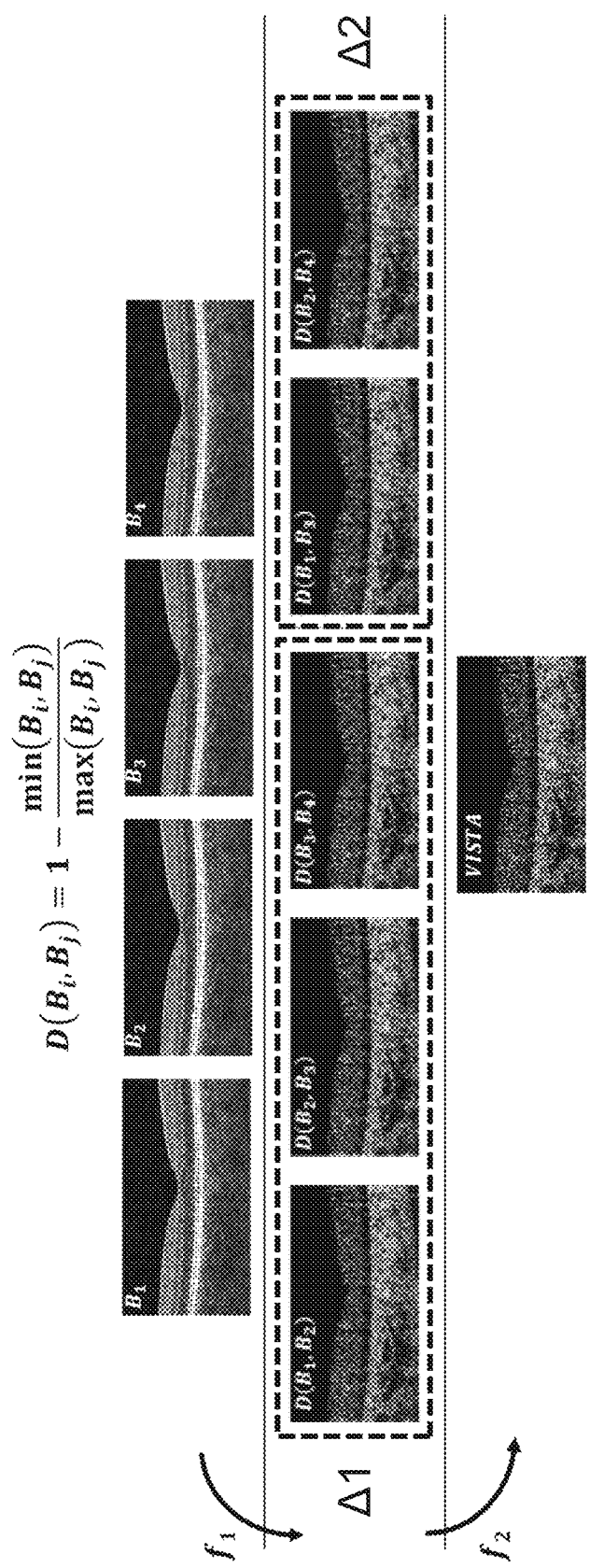

FIGS. 8 and 9 schematically show a first example VISTA function according to the above; and FIGS. 10 and 11 show a second example VISTA function according to the above. In particular, the second example differs in that the function $f_2$ is not invariant to permutations of the non-$\Box$ elements of C. In other words, with reference to the second example in FIGS. 10 and 11, swapping one of the intermediate OCT-A images in the dashed box Δ1 for one in the dashed box Δ2 changes the output of $f_2$; but swapping images within the same box does not affect the output. Alternatively stated, each pair-wise B-scan comparison is not treated identically in forming the final output.

With reference to the first example of FIGS. 8 and 9, a set of three raw OCT B-scans $(B)_i$ are transformed into OCT-A images according to an initial function $f_1$, representing the decorrelation between compared images. Here, the initial function $f_1$ can be provided as $$D(B_i, B_j) = 1 - \frac{\min(B_i, B_j)}{\max(B_i, B_j)},$$

where D represents the OCT-A image and B represents the raw OCT B-scan. This transformation yields the matrix C of OCT-A images D, formed by the transformation $f_1$. Each image D in the matrix C can be combined to form a single representative image. Such a combination could be, for example, any statistical computation such as a sum or average of the images D therein. In the example illustrated in FIGS. 8 and 9, the combination is defined as $$f_2(C) = \frac{\frac{1}{2}(C_{1,2} + C_{2,3})}{C_{1,3}}.$$

As illustrated in FIG. 9, two different permutations P, P' of the matrix C applied to the second transformation $f_2$ do not result in the same combined image.

Similarly, the second example of FIGS. 10 and 11 begins with a set of four raw OCT B-scans ($B_1$-$B_4$) that are transformed into OCT-A images according to an initial function $f_1$, representing the decorrelation between compared images. Here, the initial function $f_1$ can be provided as $$D(B_i, B_j) = 1 - \frac{\min(B_i, B_j)}{\max(B_i, B_j)},$$

where D represents the OCT-A image and B represents the raw OCT B-scan. This transformation yields a set of OCT-A images $\Delta_1$ representing an interscan time of $\Delta t$ (e.g., 1.5 ms) and a set of OCT-A images $\Delta_2$ representing an interscan time of $2\Delta t$ (e.g., 3 ms).

As shown in FIG. 11, the transformation $f_1$ yields a matrix C, where each image D in the set of images $\Delta_1$ and each image D in the set of images $\Delta_2$ corresponds to a diagonal of the matrix C. Each of the sets of images $\Delta_1$ and $\Delta_2$ can be combined by a second function $f_2$ to form a single representative VISTA image. Such a combination could be, for example, any statistical computation such as a sum or average of the images D therein. In the example illustrated in FIG. 11, the combination is defined as $$f_2(c) = \frac{\frac{1}{3}\Sigma\Delta 1 \text{ set}}{\frac{1}{2}\Sigma\Delta 2 \text{ set}},$$

representing a ratio of the average of the images in each set. The numerator represents a combined image of the $\Delta_1$ set (an image for the interscan time associated with $\Delta_1$) and the denominator represents a combined image of the $\Delta_2$ set (an image for the interscan time associated with $\Delta_2$).

According to the above examples, the repeated OCT B-scans and OCT-A B-scans at any B-scan position were treated as independent from the OCT B-scans and OCT-A B-scans at other B-scan positions in the volume. However, an analogous analysis can be applied to when volumetric transformations and/or filterings of the inputted OCT and/or OCT-A data are applied prior to, during, and/or after VISTA processing. For example, the volumetric OCT-A data of the same interscan time may be averaged and projected through depths of interest (for example, through the depths spanned by the retinal vasculature) to form en face images (here each B-scan location corresponds to a line in the en face image). The projection may be, for example, a mean projection, median projection, minimum projection, maximum projection, or mean-of-ranks projection. The en face images may be filtered prior to, during, and/or after further VISTA processing. For example, steps to remove OCT-A projection artifacts may be applied. The function $f_2$ may then be applied to these filtered, or unfiltered, en face images. As another example, OCT-A volumes corresponding to different interscan times may be formed by collecting OCT-A images from different slow-scan positions and this data may be volumetrically filtered, for example with a 3-D Gaussian, median filter, and/or vesselness filter, and then mapped to a VISTA volume using a volumetric analogue of $f_2$. Multiple VISTA images may also be averaged to improve signal-to-noise.

Other pre-processing and/or post-processing steps may be applied to compensate for patient motion. For example, two or more orthogonally, or pseudo-orthogonally, oriented volumes can be acquired. These volumes can then be registered and merged. Certain layers may also be segmented and, by adjusting, relative to some reference curve, the A-scan and/or B-scan positions and/or orientations in two-dimensional or three-dimensional space, these segmentations may be used to compensate for patient motion. A-scans and/or B-scans may also be warped or distorted in a non-rigid fashion to correct for patient motion. Areas of patient/eye motion may be detected automatically, for example, by identifying large decorrelations present through the entirety of the B-scan that do not correspond to blood flow. These areas may be removed, marked in some particular color to indicate their existence, marked in some color, transparency, or the like, to minimize their appearance, or be filled by interpolating or otherwise using surrounding data to predict their contents. Areas identified as being corrupted by patient motion may be treated specially in the VISTA computations (for example, by excluding these regions in filtering steps).

VISTA Color Mapping Methods

The output data from VISTA functions of the above methodology are not always easily interpretable in their raw form. Color-mapping the VISTA function or other similar output data can dramatically improve the interpretability of the data. For example, vasculature can be mapped according to blood flow speed, where red vasculature indicates fast blood flow and blue vasculature indicates slow blood flow. Further, because no blood cells move outside of vessels, pixels outside of the vasculature can be made fully black to increase contrast and visual perception.

Figure 13:
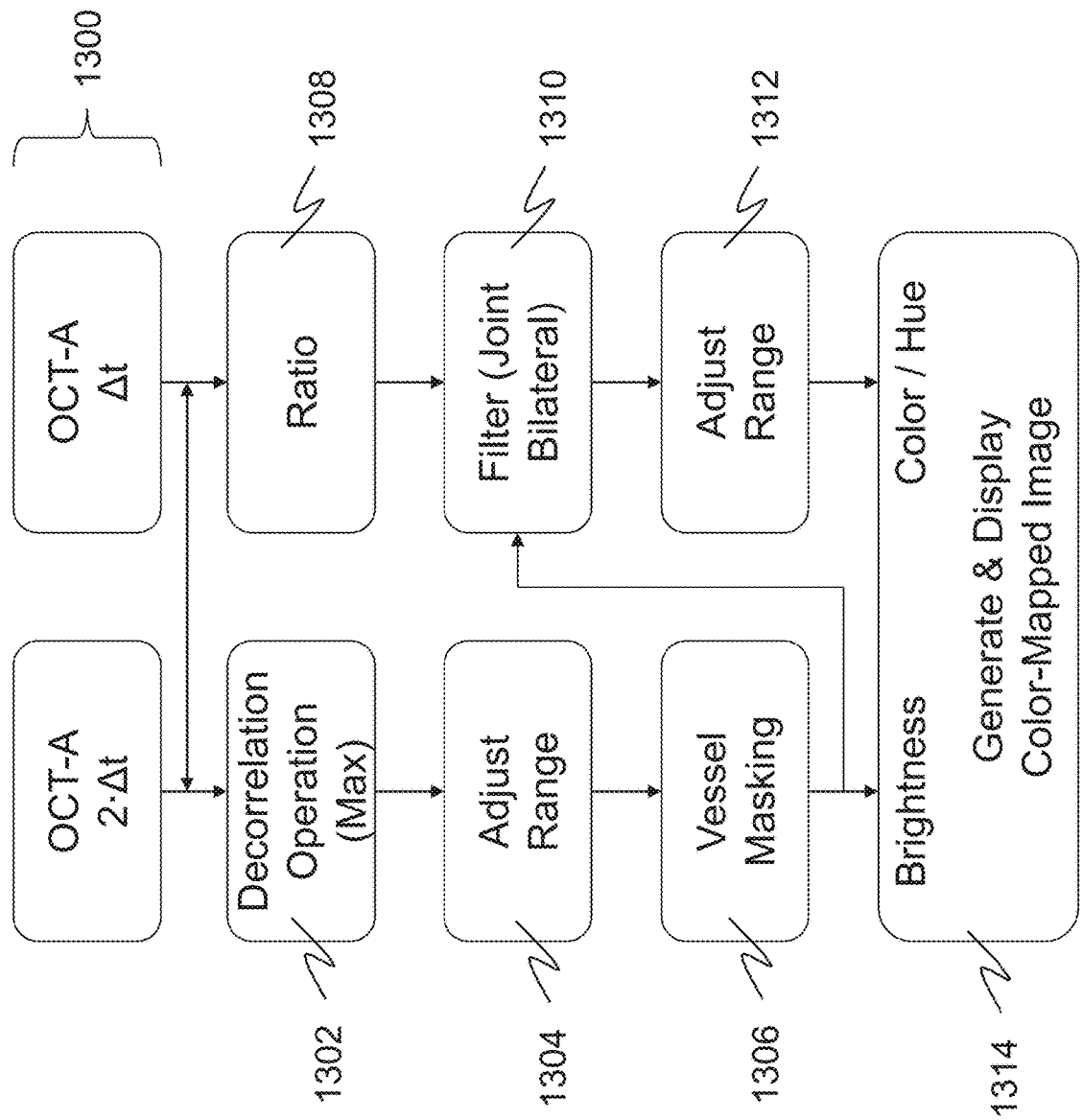
FIG. 13 is a flow chart illustrating an example method for generating a color-mapped VISTA image of FIG. 12.

Color-mapped VISTA images, for example as shown in FIG. 12, can be generated using a variety of methods. An example method is described herein and illustrated in FIG. 13. According to the method, OCT-A images corresponding to different interscan times are first computed 1300. Following the creation of the OCT-A images 1300, the process of visualizing the VISTA images can be partitioned into two, primarily parallel phases. The first phase, on the left of FIG. 13, computes the brightness value in the final color-mapped display. The brightness may, for example, be representative of the blood flux. The second phase, shown on the right of FIG. 13, computes the hue (color) in the final color-mapped display. The color may, for example, be representative of the blood flow speed. The computations in each phase may be performed pixel-by-pixel, or over patches of the images. The two phases of the display method shown in FIG. 13 are detailed below.

The generated OCT-A input images 1300 are images corresponding to two or more different interscan times. In this example, the method generates a color-mapped display based comparison of 1.5 ms interscan time ($\Delta t$) and 3.0 ms interscan time ($2\Delta t$) OCT-A input images to form the output shown in FIG. 12. Referring back to the example of FIGS. 10 and 11, it is again noted that each image D in the sets of images $\Delta_1$, $\Delta_2$ can be combined to form a single representative image of the respective interscan time. In the example illustrated in FIG. 11, the combination is defined as $$r_{\Delta 1} = \frac{1}{3}\left\{\left(1 - \frac{\min(B_1, B_2)}{\max(B_1, B_2)}\right) + \left(1 - \frac{\min(B_2, B_3)}{\max(B_2, B_3)}\right) + \left(1 - \frac{\min(B_3, B_4)}{\max(B_3, B_4)}\right)\right\}$$

$$\text{and } r_{\Delta 2} = \frac{1}{2}\left\{\left(1 - \frac{\min(B_1, B_3)}{\max(B_1, B_3)}\right) + \left(1 - \frac{\min(B_2, B_4)}{\max(B_2, B_4)}\right)\right\}.$$

Simplified, $r_{\Delta 1} = \frac{1}{3}\{D(B_1, B_2) + D(B_2, B_3) + D(B_3, B_4)\}$ and $r_{\Delta 2} = \frac{1}{2}\{D(B_1, B_3) + D(B_2, B_4)\}$. These single $r_{\Delta 1}$ and $r_{\Delta 2}$ images representing $\Delta_1$, $\Delta_2$ can then be provided as the inputs (OCT-A $2\Delta t$ and OCT-A $\Delta t$, respectively) 1300 to the method in FIG. 13. Images D based on different interscan times may also be combined to form a single representative image.

According to the brightness phase of the method in FIG. 13, the first step is to perform a decorrelation operation 1302 on the input OCT-A images. For example, this may include taking, for each pixel of the input OCT-A images, the maximum of the two input OCT-A images. It can be the case that the image formed from the larger effective interscan time (e.g., 3.0 ms) contains the higher decorrelation value; however, because of the stochastic nature of sampling, along with other factors, it can happen that the shorter interscan time (e.g., 1.5 ms) actually contains the higher decorrelation value. Other operations besides the maximum can be used for this step—for example, the mean, or median. This decorrelation operation thus generates a brightness decorrelation image, where each pixel of the brightness decorrelation image is a result of the decorrelation operation performed on the corresponding pixels of the input OCT-A images.

After the decorrelation operation 1302, the image contrast of the brightness decorrelation image is adjusted 1304, for example, by remapping the pixel intensities in the 1% and 99% quantiles to the values 0 (black) and 1 (white), to normalize the contrast. Other quantiles may be used in still other embodiments. The remaining pixel intensities are then linearly mapped between the black and white levels. Nonlinear re-mappings could also be suitable for enhancing certain aspects of the image.

In the next step vasculature of the OCT-A images is masked 1306. The cases of retinal and choriocapillaris vasculatures are handled differently. In the case of OCT-A images of the retinal vasculature, a Frangi vesselness filter, which emphasizes features of vascular morphology, can be applied to the contrast adjusted decorrelation image. Other vesselness filters, or other more general filters, may also be applied. The resulting image can then be thresholded and applied to the adjusted brightness image as binary mask, effectively setting pixels between vessels to zero. In doing so, the intercapillary noise can be significantly reduced. A vesselness filter for OCT-A images of the retinal vasculature can be used because the vessel structure can be clearly resolved using OCT-A. However, this vesselness filter may not always produce desirable for the choriocapillaris vasculature because the fine vascular choriocapillaris structure cannot be resolved with the resolution of a typical OCT system. OCT systems with finer resolutions may resolve this concern.

According to the color computation phase of the method in FIG. 13, the hue values are determined. First, the pixel-by-pixel ratio of the two input OCT-A images is calculated 1308, thereby forming a color decorrelation image, where each pixel of the color decorrelation image corresponds to the ratio of the corresponding pixels of the input OCT-A images. In calculating this ratio, OCT-A images of different interscan times cannot be interchanged without causing a change in the output. With reference to FIG. 10, a ratio corresponds to transformation $f_2$ and may be defined as $$f_2 = \frac{r_{\Delta_1}}{r_{\Delta_2}},$$

with $r_{\Delta_1}$ and $r_{\Delta_2}$ being the statistical combinations of each set of OCT-A images D described above. Because the OCT-A images D are grouped according to interscan time, re-arranging the order of the pairwise comparisons will, in general, change the output of $f_2$. In other words, with respect to FIG. 10, swapping one of the intermediate OCT-A images D in the $\Delta_1$ dashed box for one in the $\Delta_2$ dashed box changes the output of $f_2$, while swapping image order of images within each box does not affect the output. Alternatively stated, each pair-wise decorrelation is not treated identically in forming the final output. Other embodiments may utilize operations besides the ratio. For example, any VISTA function could be used.

The next involves applying a filter 1310 to the input images to smooth random fluctuations that are an inevitable consequence of the randomness inherent in blood flow and the derivative nature of the signal processing. A joint bilateral filter, rather than a conventional Gaussian filter, can be used to preserve vessel boundaries. In the case of choriocapillaris images, the weights for the filter can be derived from the adjusted maximum OCT-A image, whereas in the case of retinal images, the weights for the filter can be derived from the vesselness masked adjusted image from the vessel masking step 1306 in the brightness phase of the method. Finally the range of pixel values in each filtered input image is adjusted 1312. Because the hue value of each pixel is, in essence, a ratio of the decorrelation value obtained from the 1.5 ms interscan time to the decorrelation value obtained from the 3.0 ms interscan time, the values above unity are likely the result of a high blood flow speed. Thus ratios greater than one may be set to unity, which corresponds to the fastest displayed blood flow speed. After this adjustment, the VISTA pixels are clamped at predefined high and low values, and can be linearly remapped. Other remappings, such as those based on statistical model of the VISTA signal, could also be used. The clamping values may differ for the retinal and choroidal images and be chosen empirically to maximize the dynamic ranges. Different clamping values for the retinal and choroidal images may be chosen because the retinal and choroidal vasculatures comprise ocular blood supplies with different characteristics.

Finally, the brightness and hue images are used to generate and display 1314 a VISTA color-mapped image(s) in a pseudo-HSV (hue, saturation, and value) color space, which is modified to have a more uniform color gradient/distribution. As noted above, such an example VISTA color-mapped image is illustrated in FIG. 12. According to the convention illustrated in FIG. 12, slower blood flow speeds are in blue and faster blood flow speeds are in red. Of course, other conventions may be used as desired.

The VISTA color-mapped image may also be integrated or combined with other imaging data. For example, it may be overlaid, in a semi-transparent manner, on top of a standard OCT-A image. It may also be displayed over a standard OCT-A image in a way that allows the user to toggle on or off the color-coding. It may also be displayed alongside a standard OCT-A image in a registered way, for example with a linked/synchronized cursor.

The VISTA color-mapped image may also be combined with other color-mapping schemes, for example schemes in which the OCT-A signal is colored according to depth or layer. The VISTA color-mapped image may also be combined with a color-mapping scheme that indicates the OCT level, or thresholding level (the thresholding level is related to the OCT signal strength, and is used to eliminate regions of the image strongly affected by noise). Indicating thresholding level may be useful for alerting users as to the validity of OCT-A and/or VISTA signal at a certain region. Other color codings, for example indicating the presence or severity of disease, the density of vasculature, or the absence of vasculature, may also be combined with the color coded VISTA signal.

Corresponding System and Scanning Protocols

A system for implementing the above methods comprises an OCT scanner that is configured to acquire more than two repeated OCT B-scans in a manner consistent with forming OCT-A images; a processor configured to perform the above calculations and processing of the images; a display configured to process and display the resulting images as a color-coded image (e.g., as a volume, orthoplane volume, en face image, or B-scan image). The OCT scanner may have a 1,050 nm, 400 kHz A-scan rate, and be a swept source OCT system using a 5 repeated B-scan protocol. Galvanometer scanning mirrors or resonant scanning mirrors may be used. In order to exploit the dependency of the OCT-A signal on the interscan time, the scanning rates may be sufficiently fast so as to reduce the interscan time to a point where the OCT-A signal is not being sampled in the saturation regime of the signal. The maximum interscan time that can be fruitfully in a VISTA system depends on the speeds of the blood flows being imaged (longer interscan times can be used for slower blood flow speeds, whereas faster blood flow speeds require faster interscan times). For imaging the microvasculature of the eye, it may be the case that interscan times longer than, for example, 3 milliseconds, would not be preferred.

The OCT system used may have a single incident light source. For example, the light source may be a vertical cavity surface emitting laser (VCSEL) or other frequency swept laser sources, for example, a Fourier-domain mode locked (FDML) laser. Frequency comb or akinetic light sources may also be used. The light sources may have narrow linewidths and high sweep rates, and may be centered at a 1,050 nm wavelength. The 1,050 nm center wavelength, when compared with the 840 nm wavelength systems, enables deeper light penetration into the retinal pigment epithelium, choroid, and reduced attenuation from ocular opacities. Other wavelengths, for example, 1,310 nm, may be used, for example, for anterior eye imaging, or imaging of other tissues. Other light sources, such as super luminescent diodes, either at 840 nm wavelengths, or other wavelengths, may also be used. Spectral-domain OCT (SD-OCT) or swept-source OCT (SS-OCT) configurations may be used. The choice of light-source may be determined by a combination of axial resolution, beam absorption, scan rate, phase-stability, the type of tissues being imaged, and/or other factors.

For swept-source OCT configurations, the OCT interferometric signals can be acquired with an analog-to-digital acquisition card externally clocked at a maximum frequency of 1.1 GHz using an external Mach-Zehnder interferometer. Faster or slower clock rates may also be used. A fiber Bragg grating (FBG) may be used to stabilize the phase of the sweep. Other phase stabilization methods, such as placing reflectors in the reference and/or sample arms may be used. The card may also be clocked internally, with the signal being re-sampled linearly in wavenumber in post-processing. The signal may be collected in a polarization sensitive, or diverse configuration, and quadrature and phase information may also be detected.

OCT-A imaging may be performed over a range of field sizes, for example, 12 mm×12 mm, 9 mm×9 mm, 6 mm×6 mm, or 3 mm×3 mm, 1.5 mm×1.5 mm, or 1.0 mm×1.0 mm fields of view. Multiple field sizes may be acquired and then stitched together in post-processing, and/or eye tracking may be used to help inform the stitching. En face OCT imaging, or imaging of another modality, such as fundus photography or scanning laser ophthalmoscopy, may be used to guide the placement of the imaging fields, and/or to detect and compensate for motion. This information may be connected to the beam scanning apparatus in an open or closed loop configuration. For the different field sizes, 5 repeated B-scans from 500 uniformly spaced locations may be sequentially acquired. More or fewer repeated B-scans may be collected, and it may be possible to adjust the number of repeated B-scans collected based on the scanning field size, or other factors. Each B-scan can consist of 500 A-scans. Similarly, more or fewer A-scans may be collected, and it may be possible to adjust the number of repeated B-scans based on the field size, or other factors.

The fundamental interscan time between repeated B-scans can be, as noted above, 1.5 ms, accounting for the mirror scanning duty cycle. Other interscan times, longer or shorter, may be used. The interscan time may be adjustable based on the field size, and/or other factors. For a 1.5 ms interscan time, the acquisition time for repeated B-scans is about 7.5 ms (1.5×5) per position. With a total of 5×500×500 A-scans acquired per OCT-A volume, the total acquisition time is about 3.9 seconds. For the 6 mm×6 mm, or 3 mm×3 mm fields of view, the volumetric scan pattern yields isotropic transverse sampling of the retina at 12 micrometer and 6 micrometer intervals for the 6 mm×6 mm and 3 mm×3 mm field sizes, respectively. Smaller field sizes have proportionately more transverse sample density and provide higher OCT-A image quality. Other scanning protocol may be implemented. The quality of the VISTA image may depend on the sampling density as well as the degree to which the acquisition is oversampled.

A processor of the OCT system, or of for example, a computer which receives an output of the OCT system, can be used to perform the above described computations (for example, the computation of the VISTA function) and generate the above-described displays and images. The aspects described herein may be implemented on a processor or a plurality of processors, such as a graphics processing unit (GPU) or similar dedicated graphics processor. These processor(s) also may be embedded or integrated with other processors designed for a separate purpose, for example, as part of a central processing unit (CPU). Such processor(s) may also be for general-purpose computing on a graphics processor unit (GPGPU). A "processor" as used herein refers to any, or part of any, electrical circuit comprised of any number of electrical components, including, for example, resistors, transistors, capacitors, inductors, and the like. The circuit may be of any form, including, for example, an integrated circuit, a set of integrated circuits, a microcontroller, a microprocessor, a collection of discrete electronic components on a printed circuit board (PCB) or the like. The processor may also stand alone or be part of a computer used for operations other than processing image data. Implementation of these aspects by hardware or software may be realized in any number of electronic devices and/or applications, including but not limited to, personal computers, servers, integrated OCT or similar imaging machines, and the like. Moreover, the above aspects and/or combination of aspects may be stored in memory which is executable by one of said processors. It should also be noted that the above description is non-limiting, and the examples are but only a few of many possible processors and implementations envisioned.

It is to be noted that any of the aspects or combination of aspects described herein may be implemented via hardware or software.

Accordingly, in one example embodiment, the present invention is a computer-implemented imaging method. The method comprises: acquiring a data set representing at least three B-scan images of a same location of an object, the B-scan images separated by one or more interscan time intervals, the location having fluid moving therethrough; generating an ordered collection of pairwise comparisons of the at least three repeated B-scan images; generating one or more images based on the ordered collection of pairwise comparisons; generating a color-mapped image by mapping the one or more images to color, wherein pixel color of the color-mapped image represents a fluid flow at the location of the object; and displaying the color-mapped image. In various aspects of this embodiment, the one or more images represent a motion contrast of the location of the object; at least one of the one image is a composite of two or more pairwise comparisons; and a rearrangement or permutation of an order of the collection of pairwise comparisons changes the one or more images.

In another example embodiment, the present invention is a system for processing data sets. The system comprises a data acquisition module, configured to acquire a data set representing at least three B-scan images of a same location of an object, the B-scan images separated by one or more interscan time intervals, the location having fluid moving therethrough; a computing module, configured to: (1) generate an ordered collection of pairwise comparisons of the at least three repeated B-scan images; (2) generate one or more images based on the ordered collection of pairwise comparisons, wherein (a) the one or more images represent a motion contrast of the location of the object; (b) at least one of the one image is a composite of two or more pairwise comparisons; and (c) a rearrangement or permutation of an order of the collection of pairwise comparisons changes the one or more images; and (3) generate a color-mapped image by mapping the one or more images to color, wherein pixel color of the color-mapped image represents a fluid flow at the location of the object; and a displaying module, configured to display the color-mapped image.

In a further example embodiment, the present invention is a non-transitory computer-readable medium having thereon a sequence of instructions, which, when executed by a processor cause an imaging device to acquire a data set representing at least three B-scan images of a same location of an object, the B-scan images separated by one or more interscan time intervals, the location having fluid moving therethrough; cause the processor to: (1) generate an ordered collection of pairwise comparisons of the at least three repeated B-scan images; (2) generate one or more images based on the ordered collection of pairwise comparisons, wherein: (a) the one or more images represent a motion contrast of the location of the object; (b) at least one of the one image is a composite of two or more pairwise comparisons; and (c) a rearrangement or permutation of an order of the collection of pairwise comparisons changes the one or more images; and (3) generate a color-mapped image by mapping the one or more images to color, wherein pixel color of the color-mapped image represents a fluid flow at the location of the object; and cause a display to display the color-mapped image.

Various aspects of these embodiments are as described hereinabove with respect to other example embodiments.

RESULTS AND EXAMPLES

FIGS. 14-18 illustrate various comparative examples of traditional OCT-A images and color-mapped VISTA images generated using particular implementations of VISTA analysis consistent with the above-described methods and systems.

Figure 14:
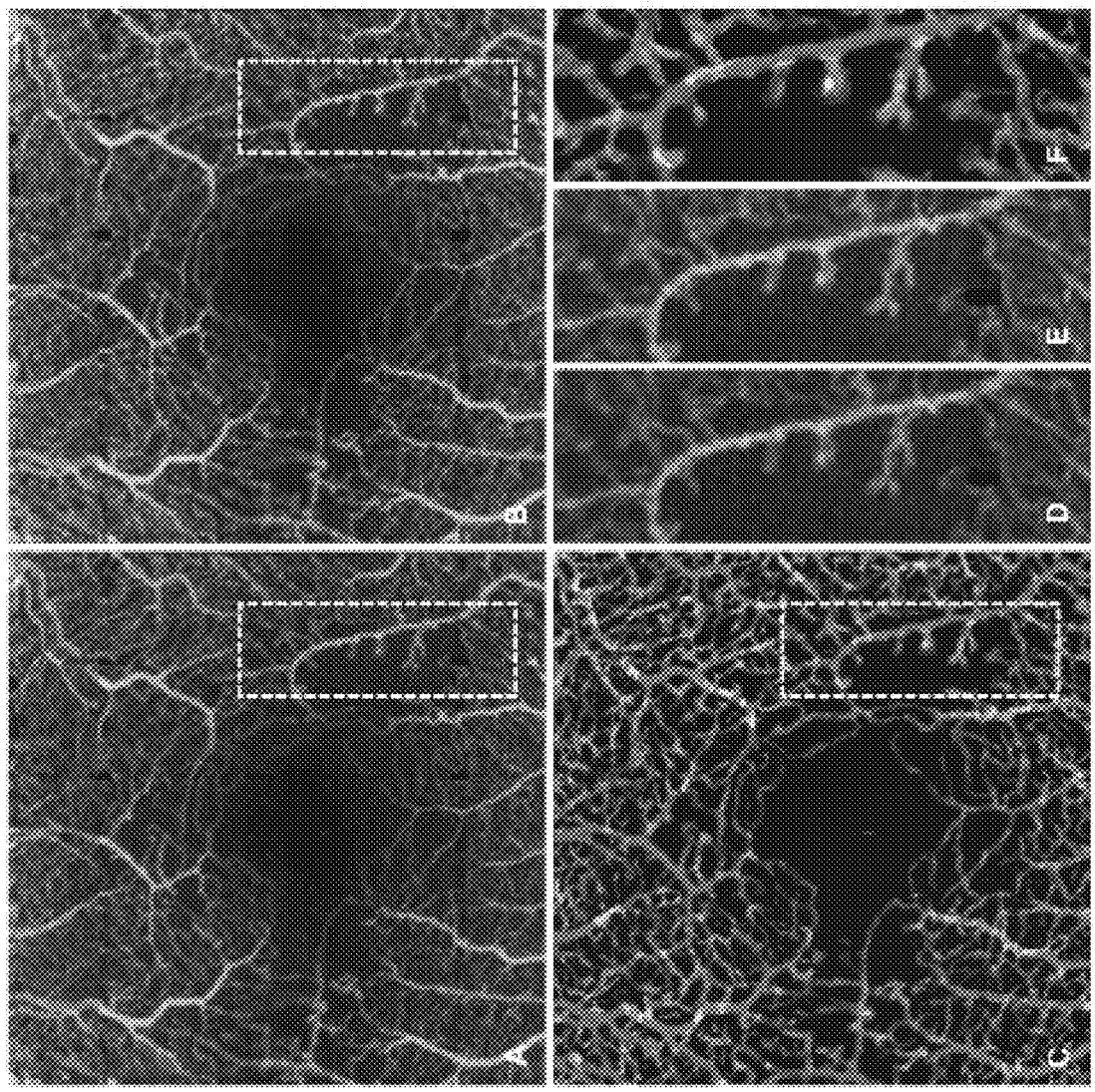
FIGS. 14A through 14F illustrate comparative examples of traditional OCT-A images and color-mapped VISTA images generated according to the description herein.

FIG. 14 illustrates images of a 53-year-old patient with nonproliferative diabetic retinopathy taken over a 3 mm×3 mm field of view. Panel A illustrates a mean projection of the 1.5 milliseconds OCT-A volume through the depths spanned by the retinal vasculature. Panel B illustrates a mean projection of the 3.0 milliseconds OCT-A volume through the depths spanned by the retinal vasculature. Panel C illustrates a color-mapped VISTA image. Panels D-F are enlargements of the dashed boxes in Panels A-C, respectively. It is noted that capillary loops, which likely correspond to microaneurysms, are associated with slower blood flow speeds. Note that this suggests that the VISTA signal may be used to detect, manually or automatically, vascular alterations associated with disease.

Figure 15:
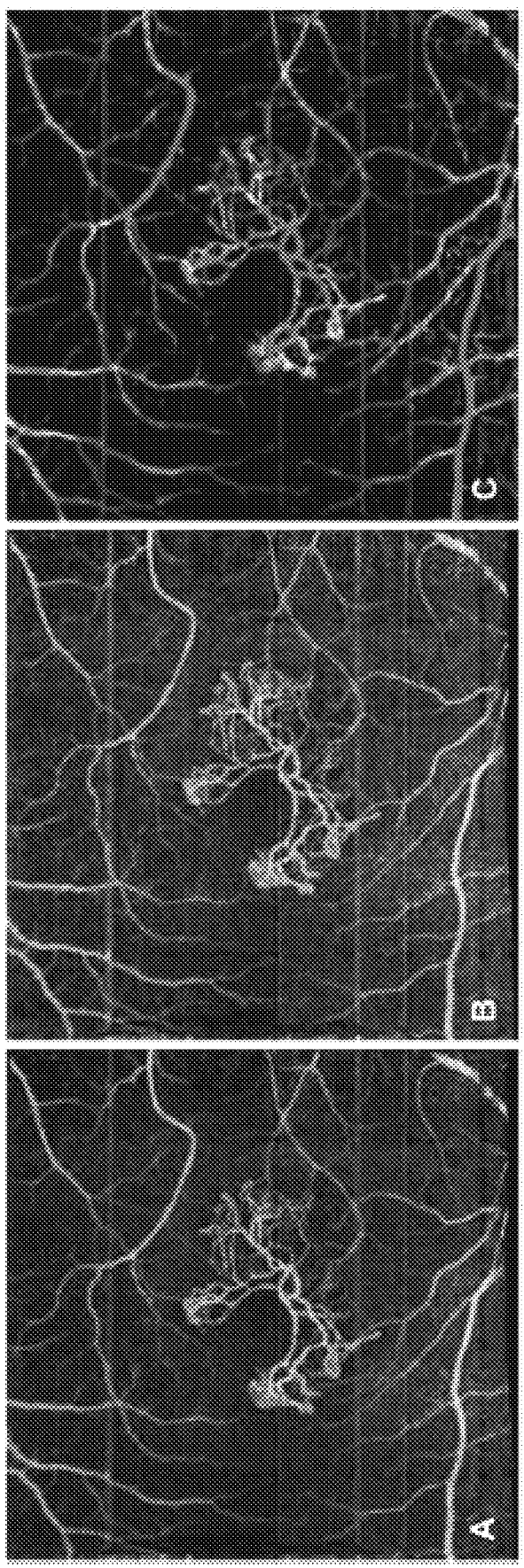
FIGS. 15A through 15C illustrate comparative examples of traditional OCT-A images and color-mapped VISTA images generated according to the description herein.

FIG. 15 illustrates images of a 90-year-old exudative patient with age-related macular degeneration, with a treated choroidal neovascular lesion, taken over a 6 mm×6 mm field of view. Panel A illustrates a mean projection of the 1.5 milliseconds OCT-A volume through the depths spanned by the lesion. Panel B illustrates a mean projection of the 3.0 milliseconds OCT-A volume through the depths spanned by the lesion. Panel C illustrates a color-mapped VISTA image. It is noted that retinal vessels generate decorrelation tails in the image. These may be suppressed or removed using projection artifact removal techniques.

Figure 16:
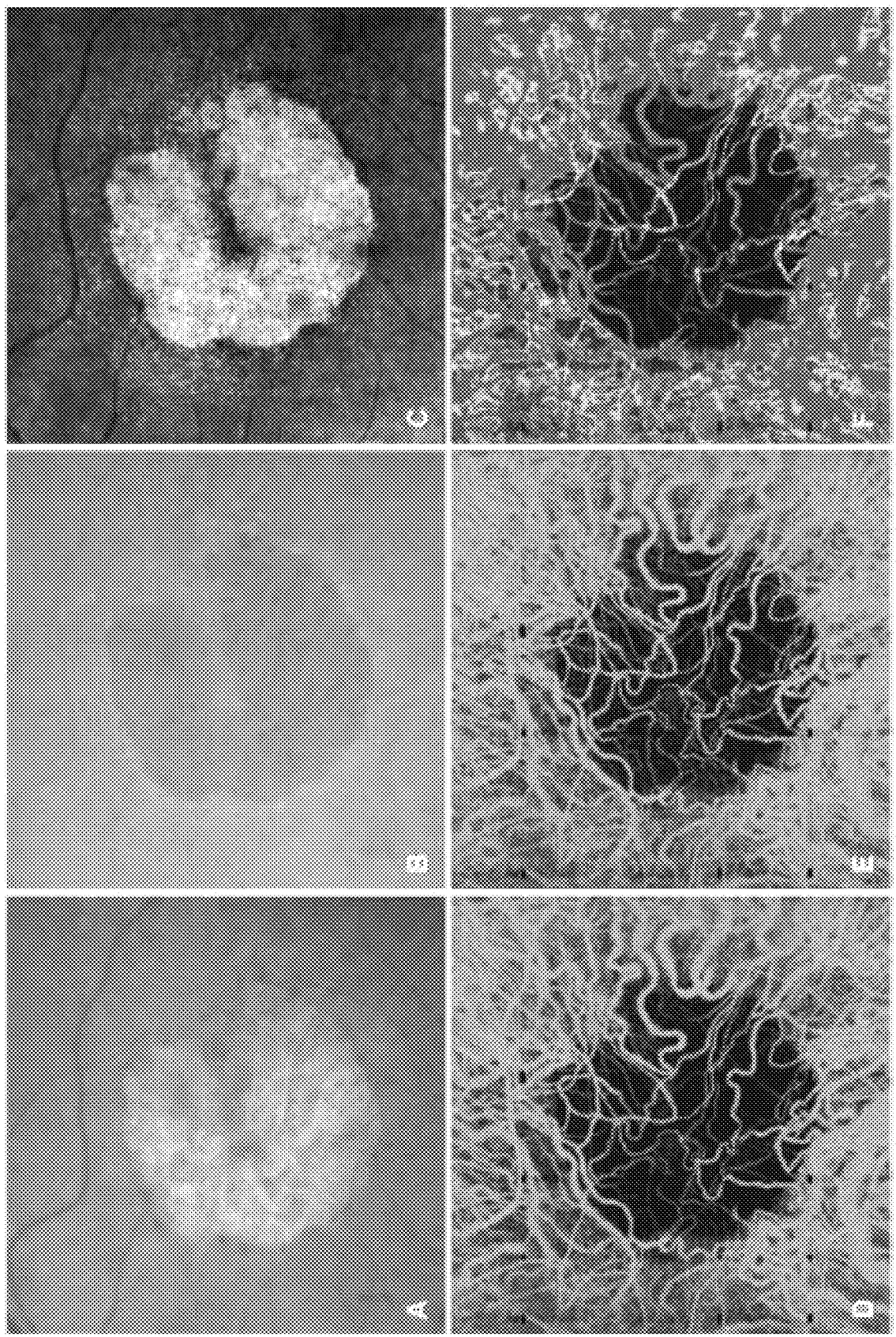
FIGS. 16A through 16F illustrate comparative examples of traditional OCT-A images and color-mapped VISTA images generated according to the description herein.

FIG. 16 illustrates images of a 75-year-old patient with geographic atrophy taken over a 6 mm×6 mm field of view. Panel A illustrates a fundus photograph, cropped over the OCT field of view. Panel B illustrates a fundus autofluorescence, cropped over the OCT field of view. Panel C illustrates a mean en face projection of the entire OCT volume. Panel D illustrates a mean projection of the 1.5 milliseconds OCT-A volume through ~90 micrometer slab, lying below the Bruch membrane. Panel E illustrates a mean projection of the 3.0 millisecond OCT-A volume through ~90 micrometer slab, lying below the Bruch membrane. Panel F illustrates a color-mapped VISTA image. It is noted that the OCT volume was not flattened and therefore, because of the curvature of the retina, the ~90 micrometer slab, while lying roughly near where the Bruch membrane would be located near the center of the field of view, intersects deeper choroidal vasculature on the edges of the image. It is further noted that the readily visible choroidal vessels in the region of atrophy show a distribution of blood flow speeds. Also of note, on the left of the margin of the image, appearing green, there is an area of relatively slow blood flow speed. This is indicative of choriocapillaris flow impairment on the geographic atrophy margin.

Figure 17:
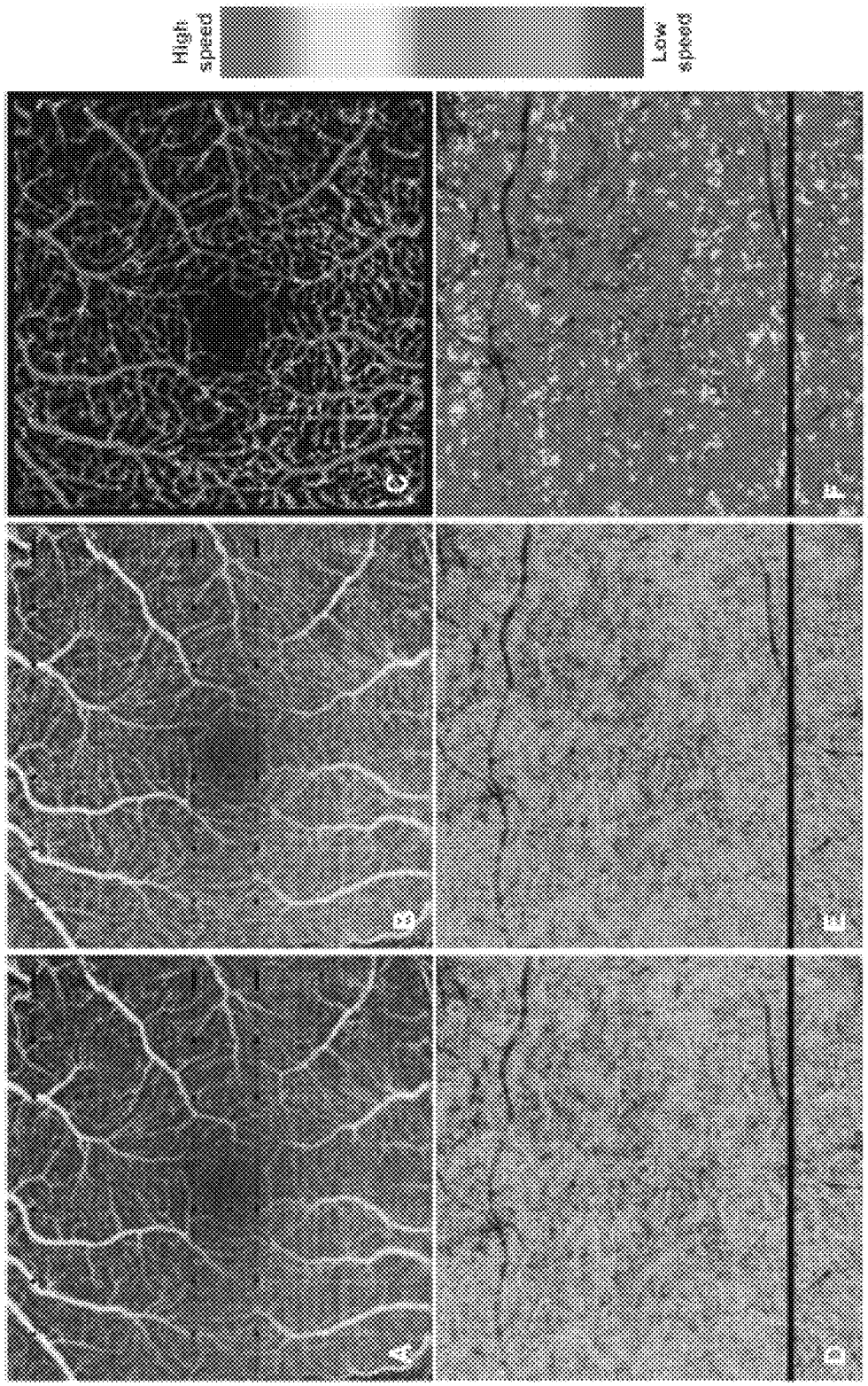
FIGS. 17A through 17F illustrate comparative examples of traditional OCT-A images and color-mapped VISTA images generated according to the description herein.

FIG. 17 illustrates images of a 43-year-old normal patient, taken over (Panels A-C) a 3 mm×3 mm field of view, and (Panels D-F) a 6 mm×6 mm field of view. Panel A illustrates a mean projection of the 1.5 milliseconds OCT-A volume through the depths spanned by the retinal vasculature. Panel B illustrates a mean projection of the 3.0 milliseconds OCT-A volume through the depths spanned by the retinal vasculature. Panel C illustrates a color-mapped VISTA image—red indicating faster blood flow speeds, and blue indicating slower speeds. The blood flow speed gradient is noted, with the larger retinal vessels associated with faster speeds, and the smaller retinal vessels associated with slower speeds. Panel D illustrates a mean projection of the 1.5 milliseconds OCT-A volume through ~90 micrometer slab, lying below the Bruch membrane. Panel E illustrates a mean projection of the 3.0 milliseconds OCT-A volume through ~90 micrometer slab, lying below the Bruch membrane. Panel F illustrates a color-mapped VISTA image. Homogenous speed in the choriocapillaris vasculature is noted.

Figure 18:
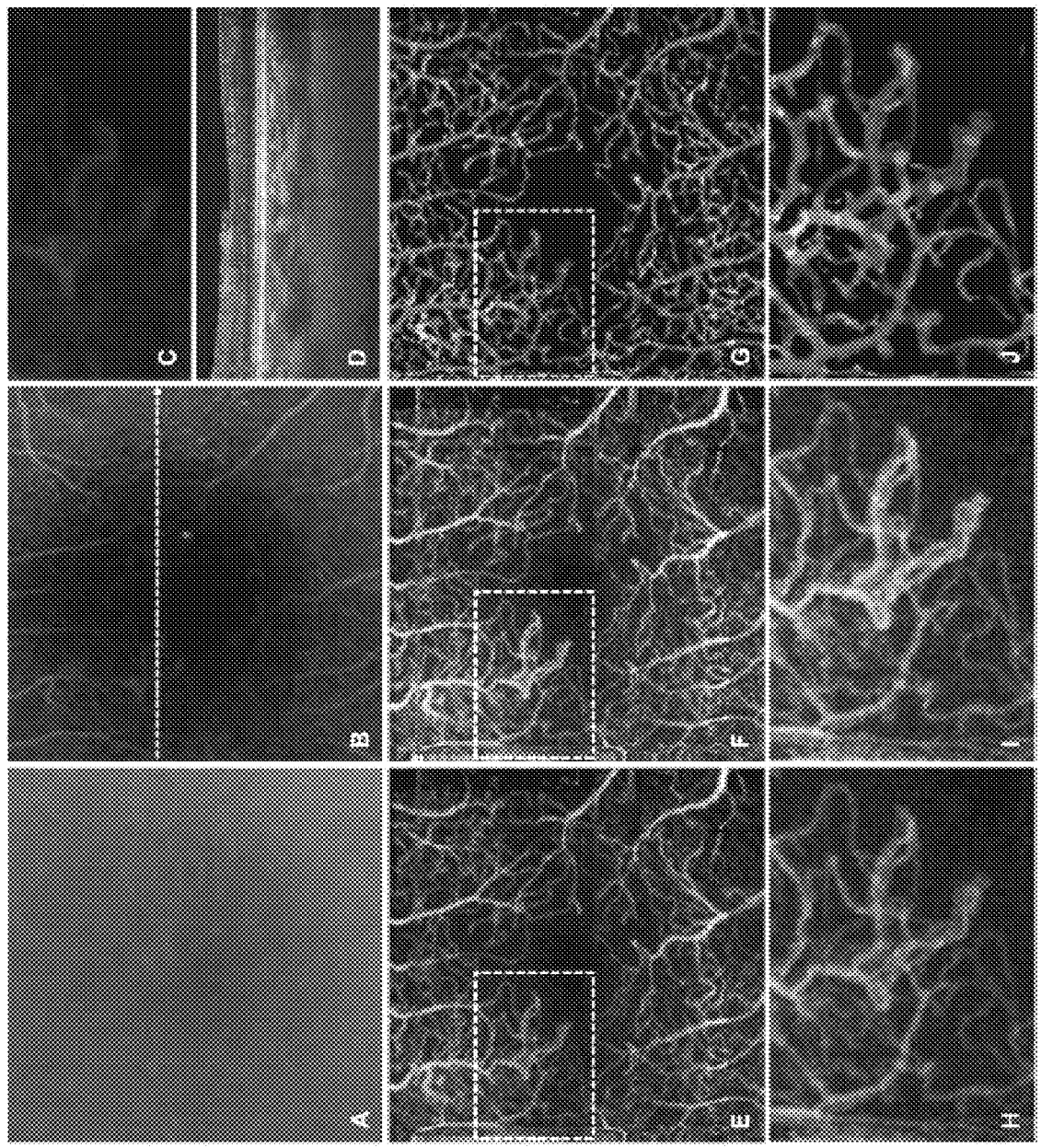
FIGS. 18A through 18J illustrate comparative examples of traditional OCT-A images and color-mapped VISTA images generated according to the description herein.

FIG. 18 illustrates images of a 30-year-old patient with proliferative diabetic retinopathy taken over a 3 mm×3 mm field of view. Panel A illustrates a fundus photograph, cropped over the OCT field of view. Panel B illustrates fluorescein angiography, cropped over the OCT field of view. Panel C is an enlargement of the fluorescein angiography image about the neovascular lesion. Panel D illustrates an OCT B-scan taken through the dashed line in Panel B. The neovascular lesion is seen lying above the retina. Panel E illustrates a mean projection of the 1.5 millisecond OCT-A volume through the depths spanned by the retinal vasculature. Panel F illustrates a mean projection of the 3.0 millisecond OCT-A volume through the depths spanned by the retinal vasculature. Panel G illustrates a color-mapped VISTA image. Panels H-J are enlargements of the dashed boxes in Panels E-G, centered on the neovascular lesion. It is noted that the lesion is associated with slower blood flow speeds.

In sum, the above methods and systems were evaluated on normal control eyes (n=2; mean age=48.0±7.1), eyes with nonproliferative diabetic retinopathy, (n=6; mean age=56.7±7.3), eyes with proliferative DR (n=3; mean age=49.4±4.4), eyes with geographic atrophy (n=4; mean age=78.2±2.8), and exudative patients with age-related macular degeneration (n=2; mean age=84.5±7.8). In controls, a blood flow speed gradient is observed, with higher speeds associated with the larger retinal vasculatures and slower speeds associated with smaller vessels. In patients with NPDR, slower speeds associated with capillary looping are observed, and in patients with PDR, slower speeds associated with neovascular lesions are observed. In patients with geographic atrophy, a distribution of blood flow speeds associated within the choroidal vessels underlying the region of atrophy is observed. Lower blood flow speeds in certain areas in and beyond the margins of atrophy are also observed. In patients with exudative age-related macular degeneration, a distribution of speeds associated with the lesions, with faster speeds being associated with the trunk of the lesion and slower speeds associated with the lesion extremities is observed.

CONCLUSION

The ability to visualize blood flow speed changes—as opposed to simply the presence or absence of blood flux—can be valuable for studying a variety of ocular diseases. This can be particularly true for those whose pathogenesis proceeds through different stages of flow impairment rather than an immediate progression to total vascular atrophy. Images generated according to the above methods and systems can, for example, be used to investigate markers for disease progression, or early disease detection. Previous methods were limited by a lack of an effective method of integrating, quantifying, and viewing VISTA data. The methods presented here, which involve a concatenated pipeline of scanning protocols and devices consistent with VISTA, systems and methods for performing VISTA functions, and systems and methods for displaying the output of VISTA functions address this limitation. In particular, this limitation is addressed by mapping the raw VISTA data using a VISTA function, and then mapping the output of the VISTA function into an easily interpretable color space.

For example, the outputs of the VISTA function and/or the color-mapped images may be used to compute a single number, or a set of numbers, from the pixels therein. These numbers may represent and provide a measure of blood flow speed in various vasculature of the eye (e.g., the average blood flow speed, or the variance in blood flow speeds). This information can be used to grade a level of ocular disease. Similarly, pixels in the VISTA and/or color-mapped images can be identifying as belonging to regions of abnormal vasculature when they have abnormal values. The pixel values may be deemed abnormal based on comparisons to normative databases, predefined thresholds, comparisons to images of a same patient generated over a period of time (e.g., months or years, identifying disease progression), and the like. The number of abnormal features, the area of the abnormal features, the average flow speed of the abnormal images, or an image highlighting the detected abnormal features can be determined and/or displayed by comparing all (or sets of) identified pixels collectively. In still another example, abnormal microaneurysms may be identified and output as those regions whose pixel values are lower than expected in a normal state. Again, the abnormal regions may be identified by comparison to normative databases, predefined thresholds, or comparison to a same patient over time; and the information.

While the above example images use two different interscan times—1.5 ms and 3.0 ms—it should be noted that the method is extendable to an arbitrary number of different interscan times. In general, as more interscan times are added, a finer gradation of blood flow speeds is appreciable. However, as the total scan time increases, the likelihood of patient motion accumulating between repeated B-scans also increases, which can have a deleterious effect on image quality. Accurate motion correction methods, for example through hardware-based eye tracking, computational post-processing, or a combination thereof, can help to reduce patient motion artifacts. The usage of smaller interscan times can also mitigate effects of patient motion, and also may lend itself to improved quantitation of the VISTA signal in that it samples the blood cell position more frequently as the blood cell passes through the OCT beam (analogous to the concept of sampling a signal at a rate greater than the Nyquist rate so as to avoid aliasing). Reducing the fundamental interscan time also has the advantage of allowing higher speed blood flows to be resolved, such as those that may occur in larger vasculature. Reducing the fundamental interscan time may require improved galvanometer scanning performance, or other scanning technology, for example resonant scanners, and, if the same fields and sampling densities are desired, increased A-scan rates.

Relative to varying the inter A-scan time (within a single acquisition) and displaying a color map representing blood flow speed, the present method uses repeated B-scan acquisition. In Doppler OCT the beam is typically not repeatedly scanned at the same position. Instead, an object is densely scanned and neighboring A-scans are used to compute flow information. Furthermore, phase information is not necessarily used in VISTA analysis (i.e., simply the amplitude, or related quantities, of the OCT signal may be used). Comparing adjacent A-scans versus every-other A-scan is not equivalent to comparing adjacent B-scans versus every-other B-scan because the former involves a spatial skip, while the latter involves only a temporal skip. In dual beam Doppler OCT, the acquisition is markedly different because there are two OCT beams, not one. Further, varying the inter B-scan time has not been done within a single acquisition and then mapped into images in a manner consistent with the methods and protocols described above. Furthermore, using different scan patterns for different interscan times is not the same as the methods presented herein.

For example, varying the inter B-scan within a single acquisition of repeated OCT B-scans may be important for many reasons including that it supports spatial registration of the OCT-A images corresponding to different interscan times and that it samples the same stochastic process (i.e., the OCT measurements sample the event of a blood cell, or blood cells, passing through the OCT beam). If different acquisitions of repeated B-scans are used to study the effects of the interscan time then the resulting images may not be spatially aligned; furthermore, the OCT B-scans corresponding to different acquisitions of repeated B-scans are not sampling the same process (e.g., different blood cells are passing through the OCT B-scans). The latter point makes such multiple acquisitions ill-suited to statistical analyses. In contrast, VISTA acquisitions are well suited to the application of statistical analyses, for example using dynamic light scattering theory and/or related techniques.

In contrast to traditional OCT-A acquisition, the present method forms sets of intermediate OCT-A images (formed by pairwise comparison) and then maps these into image(s) using a VISTA function. Whereas traditional OCT-A methods do not care about the "ordering" of the intermediate images, treating them all the same, the output of the method described herein is dependent upon the "order," and uses this dependency to estimate blood flow speed and/or related quantities. Further, standard OCT-A does not provide for the techniques for mapping the VISTA function into a color space where elements of this color space are explicitly related to blood flow speed.

While this disclosure is based on the OCT imaging modality, it is not limited to OCT. For example, it is applicable to ultrasound as well. It should also be noted that while the technique described herein is related to angiography for retinal and choroidal vessel visualization, the technique is not limited in this manner either; rather, it may be applied to other visualizations of the eye (for example, visualization of vasculature in the anterior eye), or of other organs, for example in endoscopic applications, or in cardiology applications, or for studying the reperfusion of kidneys, or for evaluating the success of vascular anastomoses. The technique may also be applied to study the speed of other biological fluids besides blood, for example, the fluid of the lymphatic system. The technique may be used in humans, or in laboratory animals, and may also be used to study flow speeds of biological substances in vitro or ex vivo (for example, measuring the speed of cells in flow cytometry; or, for example, measuring the speeds of cells, nutrients, or other substances in cell culture or lab-on-a-chip applications). The technique may also be used outside of the context of biomedical sciences, for example in studying fluid speeds in industrial manufacturing applications or food and/or beverage applications (for example, monitoring fermentation processes). The technique may also be used to measure the speed of automatized equipment, and for estimating the speed of objects and/or the environment relative to the motion of vehicles or other modes of transportation. The technique may also be used to study diffusive processes.

While various features are presented above, it should be understood that the features may be used singly or in any combination thereof. Further, it should be understood that variations and modifications may occur to those skilled in the art to which the claimed examples pertain. The examples described herein are exemplary. The disclosure may enable those skilled in the art to make and use alternative designs having alternative elements that likewise correspond to the elements recited in the claims. The intended scope may thus include other examples.

What is claimed is:

1. An imaging method comprising:
   acquiring data of at least three repeated B-scan images at a same location of an object;
   generating an ordered collection of pairwise comparisons of the at least three repeated B-scan images;
   generating one or more images based on the generated ordered collection of pairwise comparisons, wherein the one or more images represent a motion contrast of the object, and wherein a re-arrangement or permutation of an order of the collection of pairwise comparisons changes the one or more images;
   generating a color-mapped image by mapping the one or more images to color, wherein pixel color of the color-mapped image represents a motion speed at the same location of the object; and
   displaying the color-mapped image,
   wherein the acquired data is part of a volumetric data set of the object, the volumetric data set of the object being generated by repeatedly, for each location of the volumetric data set of the object:
      acquiring the data of the at least three repeated B-scan images at the same location; and
      translating an imaging beam used to capture the data to a new location.

2. The imaging method of claim 1, wherein the data of the at least three repeated B-scan images is acquired in a single scan pattern.

3. The imaging method of claim 1, wherein the data of the at least three repeated B-scan images is acquired with an optical coherence tomography system.

4. The imaging method of claim 1, wherein the data of the at least three repeated B-scan images is acquired with an optical coherence tomography system having a single incident beam.

5. The imaging method of claim 1, wherein the at least three repeated B-scans are acquired at a fixed interscan time.

6. The imaging method of claim 1, wherein the pixel color is determined by:
   calculating, on a pixel-by-pixel basis, a ratio of the one or more images;
   filtering the generated ratio; and
   remapping the filtered ratio between predetermined high and low values,
   wherein color at each pixel of the color-mapped image is based on the pixel intensities.

7. The imaging method of claim 1, wherein the color-mapped image is displayed as an overlay on a corresponding image.

8. The imaging method of claim 1, wherein the object includes vasculature and the motion contrast is of blood flow through the vasculature.

9. The imaging method of claim 8, further comprising:
   determining a value representative of ocular disease based on pixel values of the one or more images, or the color-mapped image.

10. The imaging method of claim 8, further comprising:
    identifying regions of abnormal vasculature based on the one or more images, or the color-mapped image.

11. The imaging method of claim 8, further comprising:
    identifying abnormal microaneurysms based on the one or more images, or the color-mapped image.

12. The imaging method of claim 1, wherein pixel brightness of the color-mapped image represents a motion flux at the same location of the object.

13. The imaging method of claim 12, wherein the pixel brightness is derived from the ordered collection of pairwise comparisons, and wherein the pixel brightness is unchanged by the re-arrangement or permutation of the order of the collection of pairwise comparisons.

14. The imaging method of claim 12, wherein the pixel brightness is determined by:
    performing, on a pixel-by-pixel basis, a decorrelation operation on the one or more images, thereby generating a brightness decorrelation image;
    adjusting a contrast of the brightness decorrelation image by remapping pixel intensities in predefined quantiles to an upper value or to a lower value, and remapping remaining pixel intensities to values between the upper value and the lower value; and masking structural regions of the object in the one or more images and applying the masked structural regions to the brightness decorrelation image having the adjusted contrast as a binary mask, thereby setting pixel intensities that do not correspond to vasculature to the upper value or the lower value, wherein brightness at each pixel of the color-mapped image is based on the pixel intensities.

15. An imaging method comprising:
acquiring data of at least three repeated B-scan images at a same location of an object;
generating an ordered collection of pairwise comparisons of the at least three repeated B-scans images; and
generating one or more images based on the generated ordered collection of pairwise comparisons,
wherein the one or more images represent a motion contrast of the object,
wherein a re-arrangement or permutation of an order of the collection of pairwise comparisons changes the one or more images, and
wherein the acquired data is part of a volumetric data set of the object, the volumetric dataset of the object being generated by repeatedly, for each location of the volumetric data set of the object:
acquiring the data of the at least three repeated B-scan images at the same location; and
translating an imaging beam used to capture the data to a new location.

16. The imaging method of claim 15, further comprising:
generating a color-mapped image by mapping the one or more images to color, wherein pixel color of the color-mapped image represents a motion speed at the same location of the object; and
displaying the color-mapped image.

17. The imaging method of claim 16, wherein the pixel color is determined by:
calculating, on a pixel-by-pixel basis, a ratio of the one or more images;
filtering the generated ratio; and
remapping the filtered ratio between predetermined high and low values,
wherein color at each pixel of the color-mapped image is based on the pixel intensities.

18. The imaging method of claim 16, wherein the color-mapped image is displayed as an overlay on a corresponding image.

19. The imaging method of claim 16, wherein pixel brightness of the color-mapped image represents a motion flux at the same location of the object.

20. The imaging method of claim 19, wherein the pixel brightness is derived from the ordered collection of pairwise comparisons, and wherein the pixel brightness is unchanged by the re-arrangement or permutation of the order of the collection of pairwise comparisons.

21. The imaging method of claim 19, wherein the pixel brightness is determined by:
performing, on a pixel-by-pixel basis, a decorrelation operation on the one or more images, thereby generating a brightness decorrelation image;
adjusting a contrast of the brightness decorrelation image by remapping pixel intensities in predefined quantiles to an upper value or to a lower value, and remapping remaining pixel intensities to values between the upper value and the lower value; and
masking structural regions of the object in the one or more images and applying the masked structural regions to the brightness decorrelation image having the adjusted contrast as a binary mask, thereby setting pixel intensities that do not correspond to vasculature to the upper value or the lower value,
wherein brightness at each pixel of the color-mapped image is based on the pixel intensities.

22. The imaging method of claim 15, further comprising:
generating a color-mapped image by mapping the one or more images to color, wherein pixel color of the color-mapped image represents a motion speed at the same location of the object.

23. The imaging method of claim 15, further comprising:
displaying the one or more images.

24. The imaging method of claim 15, wherein the data of the at least three repeated B-scan images is acquired in a single scan pattern.

25. The imaging method of claim 15, wherein the data of the at least three repeated B-scan images is acquired with an optical coherence tomography system.

26. The imaging method of claim 15, wherein the data of the at least three repeated B-scan images is acquired with an optical coherence tomography system having a single incident beam.

27. The imaging method of claim 15, wherein the at least three repeated B-scans are acquired at a fixed interscan time.

28. The imaging method of claim 15, wherein the object includes vasculature and the motion contrast is of blood flow through the vasculature.

29. The imaging method of claim 28, further comprising:
determining a value representative of ocular disease based on pixel values of the one or more images, or the color-mapped image.

30. The imaging method of claim 28, further comprising:
identifying regions of abnormal vasculature based on the one or more images, or the color-mapped image.

31. The imaging method of claim 28, further comprising:
identifying abnormal microaneurysms based on the one or more images, or the color-mapped image.

32. A computer-implemented imaging method, comprising:
acquiring a data set representing at least three B-scan images of a same location of an object, the B-scan images separated by one or more interscan time intervals, the location having fluid moving therethrough;
generating an ordered collection of pairwise comparisons of the at least three repeated B-scan images;
generating one or more images based on the ordered collection of pairwise comparisons, wherein:
(a) the one or more images represent a motion contrast of the location of the object;
(b) at least one of the one image is a composite of two or more pairwise comparisons; and
(c) a rearrangement or permutation of an order of the collection of pairwise comparisons changes the one or more images;
generating a color-mapped image by mapping the one or more images to color, wherein pixel color of the color-mapped image represents a fluid flow at the location of the object; and
displaying the color-mapped image,
wherein the acquired data is part of a volumetric data set of the object, the volumetric data set of the object being generated by repeatedly, for each location of the volumetric data set of the object:
acquiring the data of the at least three repeated B-scan images at the same location; and
translating an imaging beam used to capture the data to a new location.

33. A system for processing data sets, comprising:
a data acquisition module, configured to acquire a data set representing at least three B-scan images of a same location of an object, the B-scan images separated by one or more interscan time intervals, the location having fluid moving therethrough;
a computing module, configured to:
(1) generate an ordered collection of pairwise comparisons of the at least three repeated B-scan images;
(2) generate one or more images based on the ordered collection of pairwise comparisons, wherein:
(a) the one or more images represent a motion contrast of the location of the object;
(b) at least one of the one image is a composite of two or more pairwise comparisons; and
(c) a rearrangement or permutation of an order of the collection of pairwise comparisons changes the one or more images; and
(3) generate a color-mapped image by mapping the one or more images to color, wherein pixel color of the color-mapped image represents a fluid flow at the location of the object; and
a displaying module, configured to display the color-mapped image,
wherein the acquired data is part of a volumetric data set of the object, and wherein the data acquisition module is configured to acquire the volumetric data set of the object by repeatedly, for each location of the volumetric data set of the object:
acquiring the data of the at least three repeated B-scan images at the same location; and
translating an imaging beam used to capture the data to a new location.

34. A non-transitory computer-readable medium having thereon a sequence of instructions, which, when executed by a processor:
cause an imaging device to acquire a data set representing at least three B-scan images of a same location of an object, the B-scan images separated by one or more interscan time intervals, the location having fluid moving therethrough,
wherein the acquired data is part of a volumetric data set of the object, the volumetric data set of the object being generated by repeatedly, for each location of the volumetric data set of the object:
acquiring the data of the at least three repeated B-scan images at the same location; and
translating an imaging beam used to capture the data to a new location;
cause the processor to:
(1) generate an ordered collection of pairwise comparisons of the at least three repeated B-scan images;
(2) generate one or more images based on the ordered collection of pairwise comparisons, wherein:
(a) the one or more images represent a motion contrast of the location of the object;
(b) at least one of the one image is a composite of two or more pairwise comparisons; and
(c) a rearrangement or permutation of an order of the collection of pairwise comparisons changes the one or more images; and
(3) generate a color-mapped image by mapping the one or more images to color, wherein pixel color of the color-mapped image represents a fluid flow at the location of the object; and
cause a display to display the color-mapped image.

* * * * *